United States Patent
Zucherman et al.

(10) Patent No.: US 7,695,513 B2
(45) Date of Patent: Apr. 13, 2010

(54) DISTRACTIBLE INTERSPINOUS PROCESS IMPLANT AND METHOD OF IMPLANTATION

(75) Inventors: James F. Zucherman, San Francisco, CA (US); Ken Y. Hsu, San Francisco, CA (US); Charles J. Winslow, Walnut Creek, CA (US); John J. Flynn, Concord, CA (US); Steve Mitchell, Pleasant Hill, CA (US)

(73) Assignee: Kyphon SARL, Neuchatel (CH)

( * ) Notice: Subject to any disclaimer, the term of this patent is extended or adjusted under 35 U.S.C. 154(b) by 1139 days.

(21) Appl. No.: 10/850,267

(22) Filed: May 20, 2004

(65) Prior Publication Data
US 2005/0010293 A1 Jan. 13, 2005

Related U.S. Application Data

(60) Provisional application No. 60/472,817, filed on May 22, 2003.

(51) Int. Cl.
*A61F 2/44* (2006.01)
(52) U.S. Cl. .................................... 623/17.11
(58) Field of Classification Search ............... 606/60, 606/61; 623/17.11–17.16
See application file for complete search history.

(56) References Cited

U.S. PATENT DOCUMENTS

| | | |
|---|---|---|
| 2,077,804 A | 4/1937 | Morrison |
| 2,456,806 A | 12/1948 | Wolffe ......................... 33/174 |
| 2,677,369 A | 5/1954 | Knowles ....................... 128/92 |
| 3,426,364 A | 2/1969 | Lumb ................................ 3/1 |
| 3,643,658 A | 2/1972 | Steinemenan ............... 128/920 |
| 3,648,691 A | 3/1972 | Lumb .......................... 128/920 |
| 3,867,728 A | 2/1975 | Stubstad ............................ 3/1 |
| 3,875,595 A | 4/1975 | Froning ............................. 3/1 |
| 4,011,602 A | 3/1977 | Rybicki et al. |
| 4,034,418 A | 7/1977 | Jackson ....................... 3/1.911 |
| 4,219,015 A | 8/1980 | Steinemenan ............. 128/92 D |
| 4,257,409 A | 3/1981 | Bacal et al. |
| 4,309,777 A | 1/1982 | Patil ............................. 3/1.91 |
| 4,349,921 A | 9/1982 | Kuntz ................................ 3/1 |
| 4,369,769 A | 1/1983 | Edwards ...................... 128/69 |

(Continued)

FOREIGN PATENT DOCUMENTS

CA 2015507 1/1991

(Continued)

OTHER PUBLICATIONS

Minns, R.J., et al., *Preliminary Design and Experimental Studies of a Novel Soft Implant for Correcting Sagittal Plane Instability in the Lumbar Spine*, Spine vol. 22, No. 16, pp. 1818-1825, © 1997, Lippincott-Raven Publishers.

(Continued)

*Primary Examiner*—Anu Ramana
(74) *Attorney, Agent, or Firm*—Coats and Bennett, P.L.L.C.

(57) ABSTRACT

Systems and method in accordance with embodiment of the present invention can includes a distractible implant comprising a distracting insert and a body having a first part and a second part adapted to be positioned between adjacent spinous processes of cervical vertebrae. The distracting insert can be inserted into cavities of the body, thereby urging apart the first part and second part, and distracting the adjacent spinous processes.

30 Claims, 28 Drawing Sheets

U.S. PATENT DOCUMENTS

| | | | |
|---|---|---|---|
| 4,401,112 A | 8/1983 | Rezaian | 128/92 B |
| 4,455,690 A | 6/1984 | Homsy | 3/1 |
| 4,479,491 A | 10/1984 | Martin | 128/92 B |
| 4,501,269 A | 2/1985 | Bagby | 128/96 G |
| 4,502,161 A | 3/1985 | Wall | 623/18 |
| 4,553,273 A | 11/1985 | Wu | 623/18 |
| 4,554,914 A | 11/1985 | Kapp | 128/92 C |
| 4,573,454 A | 3/1986 | Hoffman | |
| 4,599,084 A | 7/1986 | Nashef | 623/16 |
| 4,599,086 A | 7/1986 | Doty | 623/17 |
| 4,604,995 A | 8/1986 | Stephens | 128/69 |
| 4,611,582 A | 9/1986 | Duff | 128/69 |
| 4,632,101 A | 12/1986 | Freedland | |
| 4,636,217 A | 1/1987 | Ogilvie | 623/17 |
| 4,643,178 A | 2/1987 | Nastari | 128/92 |
| 4,657,550 A | 4/1987 | Daher | 623/17 |
| 4,685,447 A | 8/1987 | Iversen | 128/1 R |
| 4,686,970 A | 8/1987 | Dove et al. | |
| 4,696,290 A | 9/1987 | Steffee | 128/69 |
| 4,714,469 A | 12/1987 | Kenna | 623/17 |
| 4,743,256 A | 5/1988 | Brantigan | 623/17 |
| 4,772,287 A | 9/1988 | Ray | 623/17 |
| 4,790,303 A | 12/1988 | Steffee | 128/924 M |
| 4,827,918 A | 5/1989 | Olerud | |
| 4,834,757 A | 5/1989 | Brantigan | 623/17 |
| 4,863,476 A | 9/1989 | Shepperd | |
| 4,878,915 A | 11/1989 | Brantigan | 623/17 |
| 4,904,260 A | 2/1990 | Ray | 623/17 |
| 4,904,261 A | 2/1990 | Dove | 623/17 |
| 4,913,134 A | 4/1990 | Luque | 128/69 |
| 4,923,471 A | 5/1990 | Morgan | 623/16 |
| 4,931,055 A | 6/1990 | Bumpus et al. | |
| 4,932,975 A | 6/1990 | Main | 623/17 |
| 4,936,848 A | 6/1990 | Bagby | 623/17 |
| 4,946,378 A | 8/1990 | Hirayama | 623/17 |
| 4,961,740 A | 10/1990 | Ray | 606/61 |
| 4,969,887 A | 11/1990 | Sodhi | |
| 4,969,888 A | 11/1990 | Scholten | 606/94 |
| 5,011,484 A | 4/1991 | Breard | 606/61 |
| 5,015,247 A | 5/1991 | Michelson | 606/61 |
| 5,015,255 A | 5/1991 | Kuslich | 623/17 |
| 5,026,373 A | 6/1991 | Ray | 606/61 |
| 5,035,716 A | 7/1991 | Downey | 623/17 |
| 5,047,055 A | 9/1991 | Bao | 623/17 |
| 5,055,104 A | 10/1991 | Ray | 606/61 |
| 5,059,193 A | 10/1991 | Kuslich | 606/61 |
| 5,059,194 A | 10/1991 | Michelson | 606/61 |
| 5,062,845 A | 11/1991 | Kuslich | 606/80 |
| 5,062,850 A | 11/1991 | MacMillan | 623/17 |
| 5,074,864 A | 12/1991 | Cozad | 606/54 |
| 5,084,049 A | 1/1992 | Asher et al. | 606/61 |
| 5,088,869 A | 2/1992 | Greenslade | 411/386 |
| 5,092,866 A | 3/1992 | Breard | 606/61 |
| 5,098,433 A | 3/1992 | Freedland | |
| 5,105,255 A | 4/1992 | Shannon | 357/68 |
| 5,122,130 A | 6/1992 | Keller | 606/61 |
| 5,123,926 A | 6/1992 | Pisharodi | 623/17 |
| 5,127,912 A | 7/1992 | Ray | 606/61 |
| 5,147,404 A | 9/1992 | Downey | 623/17 |
| 5,167,662 A | 12/1992 | Hayes | 606/61 |
| 5,167,665 A | 12/1992 | McKinney | 606/75 |
| 5,171,278 A | 12/1992 | Pisharodi | |
| 5,180,381 A | 1/1993 | Aust | 606/61 |
| 5,192,327 A | 3/1993 | Brantigan | 623/17 |
| 5,201,734 A | 4/1993 | Cozad et al. | |
| 5,258,031 A | 11/1993 | Salib | 623/17 |
| 5,263,953 A | 11/1993 | Bagby | 606/61 |
| 5,275,601 A | 1/1994 | Gogolewski | 606/72 |
| 5,290,312 A | 3/1994 | Kojimoto | 623/17 |
| 5,300,073 A | 4/1994 | Ray | 606/61 |
| 5,304,178 A | 4/1994 | Stahurski | 606/61 |
| 5,306,275 A | 4/1994 | Bryan | 606/61 |
| 5,306,309 A | 4/1994 | Wagner | 623/17 |
| 5,352,225 A | 10/1994 | Yuan | 606/61 |
| 5,360,430 A | 11/1994 | Lin | |
| 5,366,455 A | 11/1994 | Dove | 606/61 |
| 5,387,213 A | 2/1995 | Breard | 606/61 |
| 5,390,683 A | 2/1995 | Pisharodi | 128/898 |
| 5,391,168 A | 2/1995 | Sanders | 606/61 |
| 5,395,370 A | 3/1995 | Muller et al. | |
| 5,395,372 A | 3/1995 | Holt | 606/61 |
| 5,415,661 A | 5/1995 | Holmes | 606/69 |
| 5,437,672 A | 8/1995 | Alleyne | 606/61 |
| 5,443,514 A | 8/1995 | Steffee | 623/17 |
| 5,454,812 A | 10/1995 | Lin | 606/61 |
| 5,456,722 A | 10/1995 | McLeod | 623/13 |
| 5,458,638 A | 10/1995 | Kuslich | 623/17 |
| 5,458,641 A | 10/1995 | Ramirez Jimenez | 623/17 |
| 5,458,643 A | 10/1995 | Oka | 623/18 |
| 5,468,242 A | 11/1995 | Reisberg | 606/69 |
| 5,470,333 A | 11/1995 | Ray | 606/61 |
| 5,491,882 A | 2/1996 | Walston | 29/419.1 |
| 5,496,318 A | 3/1996 | Howland | 606/61 |
| 5,505,732 A | 4/1996 | Michelson | 606/61 |
| 5,507,745 A | 4/1996 | Logroscino | 606/61 |
| 5,507,823 A | 4/1996 | Walston | 623/21 |
| 5,514,180 A | 5/1996 | Heggeness | 623/17 |
| 5,518,498 A | 5/1996 | Lindenberg et al. | |
| 5,527,312 A | 6/1996 | Ray | 606/61 |
| 5,531,747 A | 7/1996 | Ray | 606/61 |
| 5,534,028 A | 7/1996 | Bao | 623/17 |
| 5,534,029 A | 7/1996 | Shima | 623/17 |
| 5,540,689 A | 7/1996 | Sanders | 606/61 |
| 5,549,679 A | 8/1996 | Kuslich | 623/17 |
| 5,554,191 A | 9/1996 | Lahille | 623/17 |
| 5,562,736 A | 10/1996 | Ray | 623/17 |
| 5,571,191 A | 11/1996 | Fitz | 623/17 |
| 5,577,995 A | 11/1996 | Walker | 601/120 |
| 5,584,832 A | 12/1996 | Schlapfer | 606/61 |
| 5,593,409 A | 1/1997 | Michelson | 606/61 |
| 5,601,553 A | 2/1997 | Trebing | 606/61 |
| 5,603,713 A | 2/1997 | Aust | 606/61 |
| 5,609,634 A | 3/1997 | Voydeville | 623/17 |
| 5,609,635 A | 3/1997 | Michelson | |
| 5,616,142 A | 4/1997 | Yuan | 606/61 |
| 5,623,984 A | 4/1997 | Nozaki | 164/457 |
| 5,628,756 A | 5/1997 | Barker, Jr. | 606/139 |
| 5,645,597 A | 7/1997 | Krapiva | 623/17 |
| 5,645,599 A | 7/1997 | Samani | 623/17 |
| 5,653,761 A | 8/1997 | Pisharodi | 623/17 |
| 5,658,286 A | 8/1997 | Sava | 606/61 |
| 5,665,122 A | 9/1997 | Kambin | |
| 5,672,177 A | 9/1997 | Seldin | 606/71 |
| 5,674,295 A | 10/1997 | Ray | 623/17 |
| 5,674,296 A | 10/1997 | Bryan | 623/17 |
| 5,676,702 A | 10/1997 | Ratron | 623/17 |
| 5,690,649 A | 11/1997 | Li | |
| 5,702,452 A | 12/1997 | Argenson et al. | |
| 5,702,455 A | 12/1997 | Saggar | 623/17 |
| 5,707,390 A | 1/1998 | Bonutti | |
| 5,716,416 A | 2/1998 | Lin | |
| 5,725,582 A | 3/1998 | Bevan | 623/17 |
| 5,741,261 A | 4/1998 | Moskovitz | 606/79 |
| 5,746,762 A | 5/1998 | Bass | |
| 5,755,797 A | 5/1998 | Baumgartner | |
| 5,766,251 A | 6/1998 | Koshino | 623/16 |
| 5,766,252 A | 6/1998 | Henry | 623/17 |
| 5,800,438 A | 9/1998 | Tuke | 606/90 |
| 5,810,815 A | 9/1998 | Morales | |
| 5,824,098 A | 10/1998 | Stein | 623/20 |
| 5,836,948 A | 11/1998 | Zucherman | 606/61 |
| 5,860,977 A | 1/1999 | Zucherman | 606/61 |
| 5,865,846 A | 2/1999 | Bryan | 623/17 |
| 5,876,402 A | 3/1999 | Errico | 606/61 |

| Patent | Kind | Date | Inventor | Class |
|---|---|---|---|---|
| 5,876,404 | A | 3/1999 | Zucherman | 606/61 |
| 5,879,396 | A | 3/1999 | Walston | 623/21 |
| 5,885,299 | A | 3/1999 | Winslow | 606/99 |
| 5,888,224 | A | 3/1999 | Beckers | 627/17 |
| 5,888,226 | A | 3/1999 | Rogozinski | 623/17 |
| 5,951,555 | A | 9/1999 | Rehak | 606/61 |
| 5,976,186 | A | 11/1999 | Bao | 623/17 |
| 6,001,130 | A | 12/1999 | Bryan | 623/17 |
| 6,022,376 | A | 2/2000 | Assell | 623/17 |
| 6,030,162 | A | 2/2000 | Huebner | 411/413 |
| 6,045,552 | A | 4/2000 | Zucherman | 606/61 |
| 6,045,554 | A | 4/2000 | Grooms | 606/73 |
| 6,048,204 | A | 4/2000 | Klardie | 433/174 |
| 6,048,342 | A | 4/2000 | Zucherman | 606/61 |
| 6,048,344 | A | 4/2000 | Schenk | 606/73 |
| 6,068,630 | A | 5/2000 | Zucherman | 606/61 |
| RE36,758 | E | 6/2000 | Fitz | 623/17 |
| 6,074,390 | A | 6/2000 | Zucherman | 606/61 |
| 6,090,112 | A | 7/2000 | Zucherman | 606/61 |
| 6,099,531 | A | 8/2000 | Bonutti | 606/87 |
| 6,113,639 | A | 9/2000 | Ray | 623/17.16 |
| 6,126,689 | A | 10/2000 | Brett | |
| 6,127,597 | A | 10/2000 | Beyar et al. | |
| 6,129,730 | A | 10/2000 | Bono | 606/73 |
| 6,132,464 | A | 10/2000 | Martin | 623/17 |
| 6,139,550 | A | 10/2000 | Michelson | 606/69 |
| 6,149,652 | A | 11/2000 | Zucherman | 606/61 |
| 6,152,926 | A | 11/2000 | Zucherman | 606/61 |
| 6,152,927 | A | 11/2000 | Farris | 606/69 |
| 6,156,038 | A | 12/2000 | Zucherman | 606/61 |
| 6,156,067 | A | 12/2000 | Bryan | 623/17.15 |
| 6,183,471 | B1 | 2/2001 | Zucherman | 606/61 |
| 6,190,387 | B1 | 2/2001 | Zucherman | 606/61 |
| 6,190,414 | B1 | 2/2001 | Young | 623/17.15 |
| 6,193,721 | B1 | 2/2001 | Michelson | 606/70 |
| 6,200,322 | B1 | 3/2001 | Branch | 606/96 |
| 6,206,922 | B1 | 3/2001 | Zdeblick | 623/17.11 |
| 6,214,050 | B1 | 4/2001 | Huene | |
| 6,217,580 | B1 | 4/2001 | Levin | 606/71 |
| 6,224,599 | B1* | 5/2001 | Baynham et al. | 606/61 |
| 6,224,602 | B1 | 5/2001 | Hayes | 606/69 |
| 6,224,607 | B1 | 5/2001 | Michelson | 606/96 |
| 6,228,900 | B1 | 5/2001 | Shen | 522/153 |
| 6,234,705 | B1 | 5/2001 | Troxell | 403/237 |
| 6,235,030 | B1 | 5/2001 | Zucherman | 606/61 |
| 6,238,397 | B1 | 5/2001 | Zucherman | 606/61 |
| 6,261,296 | B1 | 7/2001 | Aebi | 606/90 |
| 6,280,444 | B1 | 8/2001 | Zucherman | 606/61 |
| 6,293,949 | B1 | 9/2001 | Justis | 606/61 |
| 6,306,136 | B1 | 10/2001 | Baccelli | 606/61 |
| 6,332,882 | B1 | 12/2001 | Zucherman | 606/61 |
| 6,332,883 | B1 | 12/2001 | Zucherman | 606/61 |
| 6,336,930 | B1 | 1/2002 | Stalcup et al. | |
| 6,348,053 | B1 | 2/2002 | Cachia | |
| 6,352,537 | B1 | 3/2002 | Strnad | 606/61 |
| 6,364,883 | B1 | 4/2002 | Santilli | |
| 6,368,351 | B1 | 4/2002 | Glenn | 623/17.15 |
| 6,371,984 | B1 | 4/2002 | Van Dyke | 623/11.11 |
| 6,375,682 | B1 | 4/2002 | Fleischmann et al. | |
| 6,379,355 | B1 | 4/2002 | Zucherman | 606/61 |
| 6,383,186 | B1 | 5/2002 | Michelson | 606/69 |
| 6,395,030 | B1 | 5/2002 | Songer | 623/17.11 |
| 6,398,783 | B1 | 6/2002 | Michelson | 606/70 |
| 6,402,750 | B1 | 6/2002 | Atkinson et al. | |
| 6,402,751 | B1 | 6/2002 | Hoeck et al. | |
| 6,402,756 | B1 | 6/2002 | Ralph | 606/71 |
| 6,416,776 | B1 | 7/2002 | Shamie | 424/423 |
| 6,419,676 | B1 | 7/2002 | Zucherman | 606/61 |
| 6,419,677 | B2 | 7/2002 | Zucherman | 606/61 |
| 6,419,703 | B1 | 7/2002 | Fallin | 623/17.11 |
| 6,419,704 | B1 | 7/2002 | Ferree | |
| 6,428,542 | B1 | 8/2002 | Michelson | 606/70 |
| 6,436,145 | B1 | 8/2002 | Miller | 623/20.34 |
| 6,440,169 | B1 | 8/2002 | Elberg et al. | |
| 6,451,019 | B1 | 9/2002 | Zucherman | 606/61 |
| 6,451,020 | B1 | 9/2002 | Zucherman | 606/61 |
| 6,454,771 | B1 | 9/2002 | Michelson | 606/70 |
| 6,458,131 | B1 | 10/2002 | Ray | 606/61 |
| 6,478,796 | B2 | 11/2002 | Zucherman | 606/61 |
| 6,500,178 | B2 | 12/2002 | Zucherman | 606/61 |
| 6,514,256 | B2 | 2/2003 | Zucherman | 606/61 |
| 6,520,991 | B2 | 2/2003 | Huene | |
| 6,527,776 | B1 | 3/2003 | Michelson | 606/70 |
| 6,554,833 | B2 | 4/2003 | Levy | |
| 6,558,423 | B1 | 5/2003 | Michelson | 623/17.11 |
| 6,558,686 | B1 | 5/2003 | Darouiche | 424/423 |
| 6,565,570 | B2 | 5/2003 | Sterett | 606/69 |
| 6,565,605 | B2 | 5/2003 | Goble | 623/17.11 |
| 6,579,318 | B2 | 6/2003 | Varga | 623/17.11 |
| 6,579,319 | B2 | 6/2003 | Goble | 623/17.11 |
| 6,582,433 | B2 | 6/2003 | Yun | |
| 6,582,467 | B1 | 6/2003 | Teitelbaum et al. | |
| 6,592,585 | B2 | 7/2003 | Choi et al. | |
| 6,592,586 | B1 | 7/2003 | Michelson | 606/71 |
| 6,610,091 | B1 | 8/2003 | Reiley | 623/17.11 |
| 6,620,163 | B1 | 9/2003 | Michelson | 606/61 |
| 6,626,944 | B1 | 9/2003 | Taylor | |
| 6,645,207 | B2 | 11/2003 | Dixon et al. | |
| 6,652,527 | B2 | 11/2003 | Zucherman | 606/61 |
| 6,652,534 | B2 | 11/2003 | Zucherman | 606/102 |
| 6,669,729 | B2 | 12/2003 | Chin | 623/17.11 |
| 6,685,742 | B1 | 2/2004 | Jackson | |
| 6,695,842 | B2 | 2/2004 | Zucherman et al. | |
| 6,699,246 | B2 | 3/2004 | Zucherman | 606/61 |
| 6,699,247 | B2 | 3/2004 | Zucherman | 606/61 |
| 6,709,435 | B2 | 3/2004 | Lin | |
| 6,712,819 | B2 | 3/2004 | Zucherman | 606/61 |
| 6,712,852 | B1 | 3/2004 | Chung | 623/17.11 |
| 6,723,126 | B1 | 4/2004 | Berry | |
| 6,730,126 | B2 | 5/2004 | Boehm, Jr. et al. | |
| 6,730,127 | B2 | 5/2004 | Michelson | 623/17.16 |
| 6,733,534 | B2 | 5/2004 | Sherman | |
| 6,736,818 | B2 | 5/2004 | Perren et al. | |
| 6,746,485 | B1 | 6/2004 | Zucherman | 623/17.16 |
| 6,752,831 | B2 | 6/2004 | Sybert | 623/13.17 |
| 6,758,863 | B2 | 7/2004 | Estes et al. | |
| 6,761,720 | B1 | 7/2004 | Senegas | |
| 6,783,527 | B2 | 8/2004 | Drewry | 606/61 |
| 6,796,983 | B1 | 9/2004 | Zucherman | 606/61 |
| 6,800,670 | B2 | 10/2004 | Shen | 522/153 |
| 6,811,567 | B2 | 11/2004 | Reiley | 623/17.11 |
| 6,835,205 | B2 | 12/2004 | Atkinson et al. | |
| 6,902,566 | B2 | 6/2005 | Zucherman et al. | 606/61 |
| 6,905,512 | B2 | 6/2005 | Paes et al. | |
| 6,926,728 | B2 | 8/2005 | Zucherman et al. | 606/190 |
| 6,936,050 | B2 | 8/2005 | Michelson | 606/61 |
| 6,936,051 | B2 | 8/2005 | Michelson | 606/61 |
| 6,946,000 | B2 | 9/2005 | Senegas et al. | |
| 6,981,975 | B2 | 1/2006 | Michelson | |
| 7,011,685 | B2 | 3/2006 | Arnin et al. | |
| 7,041,136 | B2 | 5/2006 | Goble et al. | |
| 7,048,736 | B2 | 5/2006 | Robinson et al. | |
| 7,081,120 | B2 | 7/2006 | Li et al. | |
| 7,087,083 | B2 | 8/2006 | Pasquet et al. | |
| 7,097,648 | B1 | 8/2006 | Globerman et al. | |
| 7,163,558 | B2 | 1/2007 | Senegas et al. | |
| 7,201,751 | B2 | 4/2007 | Zucherman et al. | |
| 7,217,293 | B2 | 5/2007 | Branch, Jr. | |
| 7,238,204 | B2 | 7/2007 | Le Couedic et al. | |
| 7,306,628 | B2* | 12/2007 | Zucherman et al. | 623/17.11 |
| 7,377,942 | B2 | 5/2008 | Berry | |
| 7,442,208 | B2 | 10/2008 | Mathieu et al. | |
| 7,445,637 | B2 | 11/2008 | Taylor | |
| 7,476,251 | B2* | 1/2009 | Zucherman et al. | 623/17.15 |
| 7,582,106 | B2 | 9/2009 | Teitelbaum et al. | |
| 2001/0012938 | A1 | 8/2001 | Zucherman | |

| | | |
|---|---|---|
| 2001/0018614 A1 | 8/2001 | Bianchi |
| 2002/0016595 A1 | 2/2002 | Michelson |
| 2002/0022843 A1 | 2/2002 | Michelson |
| 2002/0040223 A1 | 4/2002 | Sato et al. |
| 2002/0099376 A1 | 7/2002 | Michelson |
| 2002/0128655 A1 | 9/2002 | Michelson |
| 2002/0133155 A1 | 9/2002 | Ferree |
| 2002/0143331 A1 | 10/2002 | Zucherman et al. |
| 2002/0151895 A1 | 10/2002 | Soboleski |
| 2002/0183756 A1 | 12/2002 | Michelson |
| 2002/0183757 A1 | 12/2002 | Michelson |
| 2002/0188296 A1 | 12/2002 | Michelson |
| 2003/0004572 A1 | 1/2003 | Goble |
| 2003/0028250 A1 | 2/2003 | Reiley |
| 2003/0040746 A1 | 2/2003 | Mitchell |
| 2003/0060828 A1 | 3/2003 | Michelson |
| 2003/0078668 A1 | 4/2003 | Michelson |
| 2003/0153915 A1 | 8/2003 | Nekozuka et al. |
| 2003/0181912 A1 | 9/2003 | Michelson |
| 2003/0191532 A1 | 10/2003 | Goble |
| 2003/0204259 A1 | 10/2003 | Goble |
| 2004/0006391 A1 | 1/2004 | Reiley |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0087948 A1 | 5/2004 | Suddaby |
| 2004/0097931 A1 | 5/2004 | Mitchell |
| 2004/0111154 A1 | 6/2004 | Reiley |
| 2004/0116927 A1 | 6/2004 | Graf |
| 2004/0122427 A1 | 6/2004 | Holmes |
| 2004/0127989 A1 | 7/2004 | Dooris |
| 2004/0133204 A1 | 7/2004 | Davies |
| 2004/0143268 A1 | 7/2004 | Falahee |
| 2004/0167625 A1 | 8/2004 | Beyar et al. |
| 2004/0181226 A1 | 9/2004 | Michelson |
| 2004/0181229 A1 | 9/2004 | Michelson |
| 2004/0186475 A1 | 9/2004 | Falahee |
| 2004/0186476 A1 | 9/2004 | Michelson |
| 2004/0210313 A1 | 10/2004 | Michelson |
| 2004/0210314 A1 | 10/2004 | Michelson |
| 2004/0220678 A1 | 11/2004 | Chow |
| 2004/0230201 A1 | 11/2004 | Yuan |
| 2004/0230304 A1 | 11/2004 | Yuan |
| 2004/0236334 A1 | 11/2004 | Michelson |
| 2004/0236335 A1 | 11/2004 | Michelson |
| 2004/0260397 A1 | 12/2004 | Lambrecht et al. |
| 2005/0010293 A1 | 1/2005 | Zucherman et al. |
| 2005/0027297 A1 | 2/2005 | Michelson |
| 2005/0027298 A1 | 2/2005 | Michelson |
| 2005/0049708 A1 | 3/2005 | Atkinson et al. |
| 2005/0165398 A1 | 7/2005 | Reiley |
| 2005/0203512 A1 | 9/2005 | Hawkins et al. |
| 2005/0203624 A1 | 9/2005 | Serhan et al. |
| 2005/0228391 A1 | 10/2005 | Levy et al. |
| 2005/0261768 A1 | 11/2005 | Trieu |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0136060 A1 | 6/2006 | Taylor |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0235387 A1 | 10/2006 | Peterman |
| 2006/0235532 A1 | 10/2006 | Meunier et al. |
| 2006/0241613 A1 | 10/2006 | Bruneau et al. |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0293662 A1 | 12/2006 | Boyer, II et al. |
| 2006/0293663 A1 | 12/2006 | Walkenhorst et al. |
| 2007/0043362 A1 | 2/2007 | Malandain et al. |
| 2007/0151116 A1 | 7/2007 | Malandain |
| 2007/0162000 A1 | 7/2007 | Perkins |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0233068 A1 | 10/2007 | Bruneau et al. |
| 2007/0233081 A1 | 10/2007 | Pasquet et al. |
| 2007/0233089 A1 | 10/2007 | DiPoto et al. |
| 2007/0270834 A1 | 11/2007 | Bruneau et al. |
| 2007/0276493 A1 | 11/2007 | Malandain et al. |
| 2007/0282443 A1 | 12/2007 | Globerman et al. |
| 2008/0058934 A1 | 3/2008 | Malandain et al. |
| 2008/0161818 A1 | 7/2008 | Kloss et al. |
| 2008/0262617 A1 | 10/2008 | Froehlich et al. |

FOREIGN PATENT DOCUMENTS

| | | |
|---|---|---|
| DE | 2821678 A1 | 4/1980 |
| DE | 3113142 A1 | 1/1982 |
| DE | 3922044 A1 | 2/1991 |
| DE | 4012622 C1 | 7/1991 |
| DE | 4409833 | 10/1995 |
| DE | 4414781 | 11/1995 |
| DE | 201 12 123 U1 | 9/2001 |
| DE | 101 35 771 A1 | 2/2003 |
| EP | 140790 A2 | 10/1984 |
| EP | 146347 A1 | 12/1984 |
| EP | 322334 A1 | 12/1988 |
| EP | 0307241 B1 | 12/1992 |
| EP | 0677277 A2 | 10/1995 |
| EP | 0767636 B1 | 4/1997 |
| EP | 1004276 A1 | 5/2000 |
| EP | 1138268 A1 | 10/2001 |
| EP | 1302169 A1 | 4/2003 |
| EP | 1330987 A1 | 7/2003 |
| EP | 1982664 A1 | 10/2008 |
| FR | 2623085 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2705227 | 11/1994 |
| FR | 2707864 A1 | 1/1995 |
| FR | 2717066 | 9/1995 |
| FR | 2717068 | 9/1995 |
| FR | 2717675 | 9/1995 |
| FR | 2722087 A1 | 1/1996 |
| FR | 2722088 | 1/1996 |
| FR | 2722980 A1 | 2/1996 |
| FR | 2724554 | 3/1996 |
| FR | 2725892 A1 | 4/1996 |
| FR | 2730156 A1 | 8/1996 |

| | | | |
|---|---|---|---|
| FR | 2731643 A1 | 9/1996 | |
| FR | 2775183 A1 | 8/1999 | |
| FR | 2780269 A1 | 12/1999 | |
| FR | 2782911 A1 | 3/2000 | |
| FR | 2799948 A1 | 4/2001 | |
| FR | 2806614 A1 | 9/2001 | |
| FR | 2806616 A1 | 9/2001 | |
| FR | 2816197 A1 | 5/2002 | |
| GB | 780652 | 8/1957 | |
| JP | 02-224660 | 9/1990 | |
| JP | 09-075381 | 3/1997 | |
| JP | 10-179622 | 7/1998 | |
| SU | 988281 | 1/1983 | |
| SU | 1484348 A1 | 6/1989 | |
| WO | WO 90/00037 | 1/1990 | |
| WO | WO 91/16018 | 10/1991 | |
| WO | WO 94/21185 | 9/1994 | |
| WO | WO 94/26192 | 11/1994 | |
| WO | WO 94/26193 | 11/1994 | |
| WO | WO 94/26195 | 11/1994 | |
| WO | WO 95/35067 | 12/1995 | |
| WO | WO 96/08206 A1 | 3/1996 | |
| WO | WO 96/39975 | 12/1996 | |
| WO | WO 98/20939 | 5/1998 | |
| WO | WO 98/48717 | 11/1998 | |
| WO | WO 98/55038 | 12/1998 | |
| WO | WO 99/26562 | 6/1999 | |
| WO | WO 99/40866 | 8/1999 | |
| WO | WO 99/42051 | 8/1999 | |
| WO | WO 99/56653 | 11/1999 | |
| WO | WO 99/59669 | 11/1999 | |
| WO | WO 00/04851 | 2/2000 | |
| WO | WO 00/13619 | 3/2000 | |
| WO | WO 00/13620 | 3/2000 | |
| WO | WO 00/38582 | 7/2000 | |
| WO | WO 00/44319 | 8/2000 | |
| WO | WO 00/53126 | 9/2000 | |
| WO | WO 01/26566 A1 | 4/2001 | |
| WO | WO 01/28442 A1 | 4/2001 | |
| WO | WO 01/54598 A1 | 8/2001 | |
| WO | WO 2004/047689 A1 | 8/2001 | |
| WO | WO 02/34120 A2 | 5/2002 | |
| WO | WO 02/051326 | 7/2002 | |
| WO | WO 02/085226 A1 | 10/2002 | |
| WO | WO 03/057055 A1 | 7/2003 | |
| WO | WO 03/101350 A1 | 12/2003 | |
| WO | WO 2004/047691 A1 | 6/2004 | |
| WO | WO 2004/071358 A1 | 8/2004 | |
| WO | WO 2004/084768 A2 | 10/2004 | |
| WO | WO 2004/098465 A1 | 11/2004 | |
| WO | WO 2005/009300 A1 | 2/2005 | |
| WO | WO 2005/011507 A1 | 2/2005 | |
| WO | WO 2005/044118 A1 | 5/2005 | |
| WO | WO 2005/048856 A1 | 6/2005 | |
| WO | WO 2005/110258 A1 | 11/2005 | |
| WO | WO 2006/064356 A1 | 6/2006 | |
| WO | WO 2007/034516 A1 | 3/2007 | |
| WO | WO 2007052975 A1 | 5/2007 | |

OTHER PUBLICATIONS

Waldemar Link, brochure entitled *Wirbelsäulen-Chirurgie: Instrumentarium Und Implantate Zur Wirbelsäulen-Chirurgie* (Spinal-Surgery: Instrumentation and Implants for Spinal Surgery), Waldemar Link, Hamburg, Germany.

Haruo Tsuji, et al., *Ceramic Interspinous Block (CISB) Assisted Anterior Interbody Fusion*, Journal of Spinal Disorders, vol. 3, No. 1, pp. 77-86, © 1990 Raven Press, Ltd., New York.

Richard W. Porter, MD, FRCS, FRCSE, *Spinal Stenosis and Neurogenic Claudication*, Spine vol. 21, No. 17, pp. 2046-2052, © 1996, Lippincott-Raven Publishers.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," Spine, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dispositivo Intervertebrale Ammortizzante DIAM, date unknown, p. 1.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," Spine, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instablilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Congress of Neurosurgery (EANS), Sep. 7-12, 2003, pp. 835-839, Lisbon, Portugal.

Hambly et al., "Tension Band Wiring-Bone Grafting for Spondylolsis and Spondylolisthesis," Spine, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochirugia, Advanced Peripheral Nerve Surgery and Minimal Invasive Spinal Surgery, Alexandre et al., eds., 2005, pp. 129-131, vol. 92, Suppl.

McDonnell et al., "Posterior Atlanoaxial Fusion: Indications and Techniques," Techniques in Spinal Fusion and Stabilization, Hitchon et al., eds., 1995, pp. 92-106, Ch. 9, Thieme, New York.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., 1995, pp. 79-81, Ch. 7, Thieme, New York.

Richards et al., "The Treatment Mechanism of an Interspinous Process Implant for Lumbar Neurogenic Intermittent Claudication," Spine, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," Spine, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilization Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodése", La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Mé decine de Lille.

Tecnica Operatoria Per II Posizionamento Della Protessi DIAM, date unknown, pp. 1-3.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Wallis Operative Technique: Surgical Procedure for Treatment of Degenerative Disc Disease (DDD) of Lumbar Spine, date unknown, pp. 1-24, Spine Next, an Abbott Laboratories company, Bordeaux, France.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spine Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," Spine, Jul. 1992, pp. 834-837, vol. 17, No. 7.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," Spine, 1991, pp. S298-S301, vol. 16, No. 6, Supplement.

* cited by examiner

DISTRACTIBLE INTERSPINOUS PROCESS IMPLANT AND METHOD OF IMPLANTATION

CLAIM OF PRIORITY

This application claims priority to U.S. Provisional Application, entitled CERVICAL INTERSPINOUS PROCESS DISTRACTION IMPLANT AND METHOD OF IMPLANTATION, filed May 22, 2003, Ser. No. 60/472,817, which is incorporated herein by reference.

TECHNICAL FIELD

This invention relates to interspinous process implants.

BACKGROUND OF THE INVENTION

The spinal column is a bio-mechanical structure composed primarily of ligaments, muscles, vertebrae and intervertebral disks. The bio-mechanical functions of the spine include: (1) support of the body, which involves the transfer of the weight and the bending movements of the head, trunk and arms to the pelvis and legs, (2) complex physiological motion between these parts, and (3) protection of the spinal cord and the nerve roots.

As the present society ages, it is anticipated that there will be an increase in adverse spinal conditions which are characteristic of older people. By way of example only, with aging comes an increase in spinal stenosis (including, but not limited to, central canal and lateral stenosis), and facet arthropathy. Spinal stenosis results in a reduction foraminal area (i.e., the available space for the passage of nerves and blood vessels) which compresses the cervical nerve roots and causes radicular pain. Humpreys, S. C. et al., *Flexion and traction effect on C5-C6 foraminal space*, Arch. Phys. Med. Rehabil., vol. 79 at 1105 (September 1998). Another symptom of spinal stenosis is myelopathy, which results in neck pain and muscle weakness. Id. Extension and ipsilateral rotation of the neck further reduces the foraminal area and contributes to pain, nerve root compression and neural injury. Id.; Yoo, J. U. et al., *Effect of cervical spine motion on the neuroforaminal dimensions of human cervical spine*, Spine, vol. 17 at 1131 (Nov. 10, 1992). In contrast, neck flexion increases the foraminal area. Humpreys, S. C. et al, at 1105.

Pain associated with stenosis can be relieved by medication and/or surgery. It is desirable to eliminate the need for major surgery for all individuals, and in particular, for the elderly.

Accordingly, a need exists to develop spine implants that alleviate pain caused by spinal stenosis and other such conditions caused by damage to, or degeneration of, the cervical spine. Such implants would distract, or increase the space between, the vertebrae to increase the foraminal area and reduce pressure on the nerves and blood vessels of the cervical spine.

A further need exists for development of a minimally invasive surgical implantation method for cervical spine implants that preserves the physiology of the spine.

Further, a need exists for an implant that accommodates the distinct anatomical structures of the spine, minimizes further trauma to the spine, and obviates the need for invasive methods of surgical implantation. Additionally, a need exists to address adverse spinal conditions that are exacerbated by spinal extension.

DETAILED DESCRIPTION

Interspinous Implants

Figure 1:
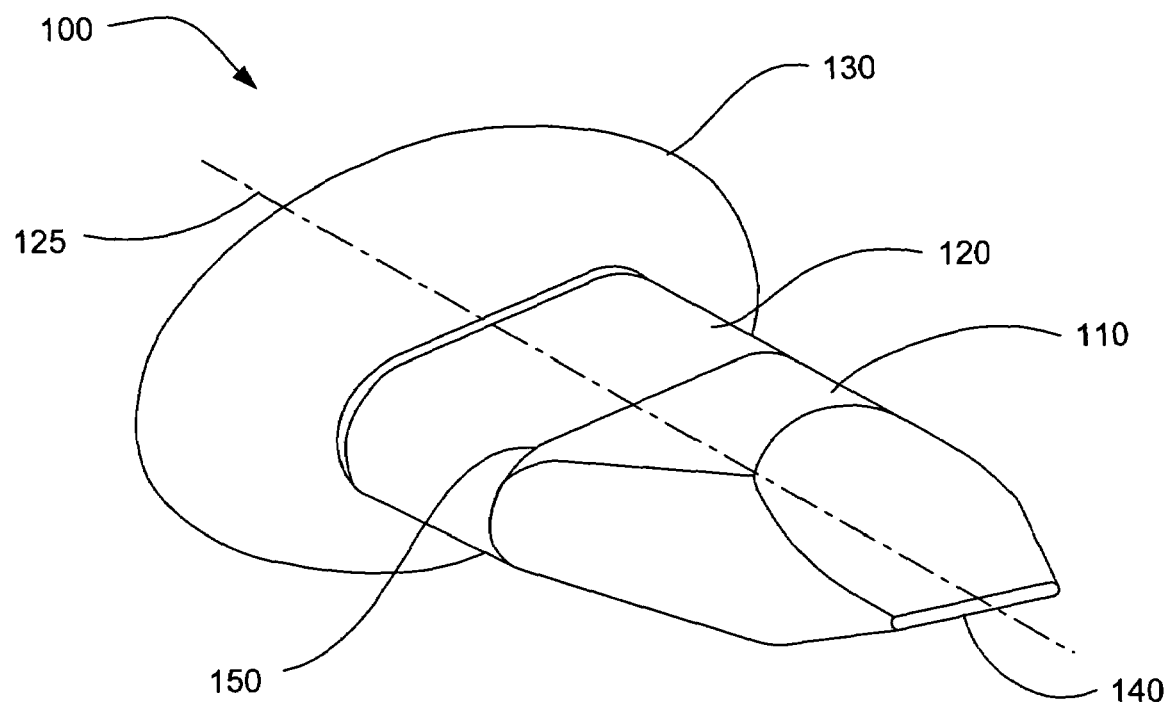
FIG. 1 is a perspective view of an embodiment of an implant in accordance with the present invention having a spacer, a distraction guide, and a wing with an elliptical cross-section.
Figure 2:
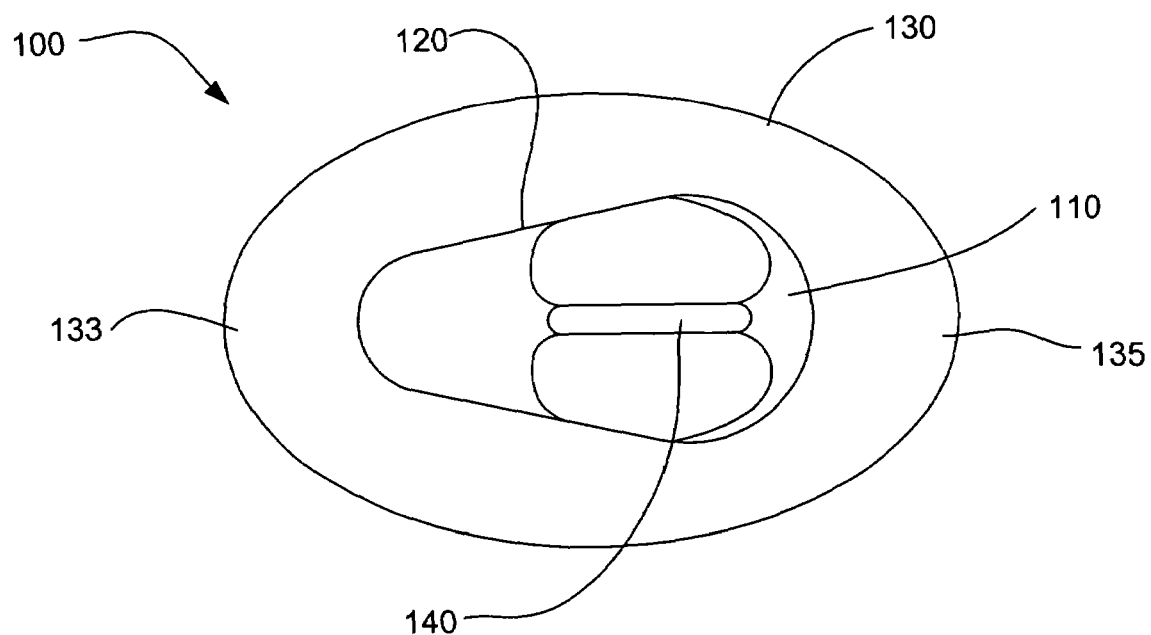
FIG. 2 is an end view of the implant of FIG. 1.

FIGS. 1 and 2 illustrate an implant 100 in accordance with an embodiment of the present invention. The implant 100 comprises a wing 130, a spacer 120, and a lead-in tissue expander (also referred to herein as a distraction guide) 110. The distraction guide 110 in this particular embodiment is wedge-shaped, i.e., the implant has an expanding cross-section from a proximal end of the implant 140 to a region 150 where the guide 110 joins with the spacer 120 (referencing for the figures is based on the point of insertion of the implant between spinous processes). As such, the distraction guide functions to initiate distraction of the soft tissue and the spinous processes when the implant 100 is surgically inserted between the spinous processes. It is to be understood that the distraction guide can be pointed and the like, in order to facilitate insertion of the implant between the spinous processes of adjacent cervical vertebrae. It is advantageous that the insertion technique disturb as little of the bone and surrounding tissue or ligaments as possible in order to reduce trauma to the site and promote early healing, and prevent destabilization of the normal anatomy. In the embodiment of FIGS. 1 and 2, there is no requirement to remove any of the bone of the spinous processes and no requirement to sever, or remove from the body, ligaments and tissues immediately associated with the spinous processes. For example, it is unnecessary to sever the ligamentum nuchae, (supraspinous ligament) which partially cushions the spinous processes of the upper cervical vertebrae.

Figure 3:
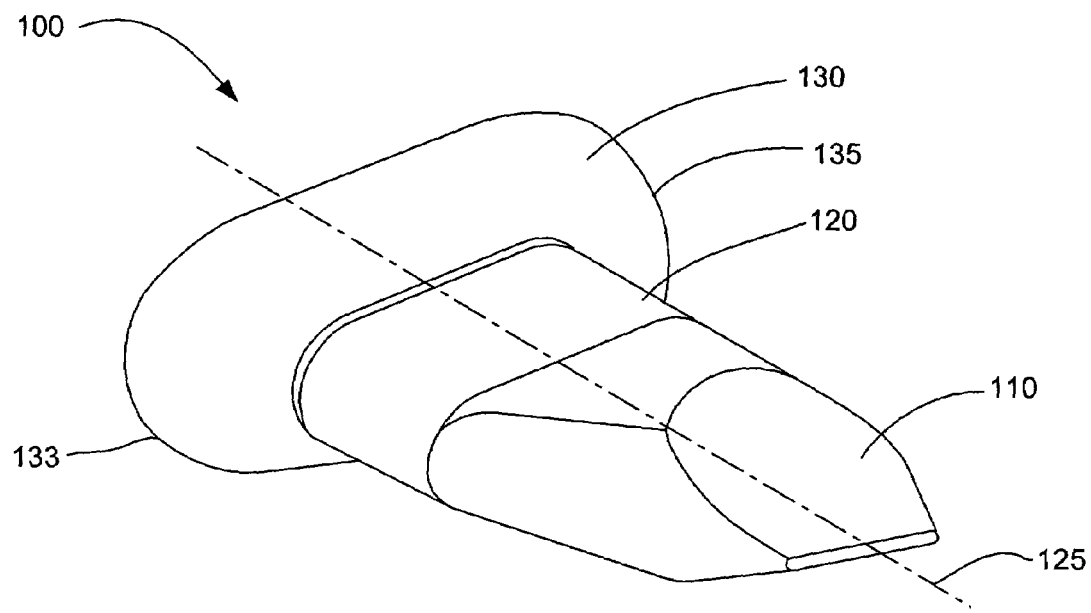
FIG. 3 is a perspective view of another embodiment of an implant in accordance with the present invention having a wing with a teardrop-shaped cross-section.

As can be seen in FIGS. 1-3, the spacer 120 can be teardrop-shaped in cross-section perpendicular to a longitudinal axis 125 of the implant. In this way, the shape of the spacer 120 can roughly conform to a wedge-shaped space, or a portion of the space, between adjacent spinous processes within which the implant 100 is to be positioned. In other embodiments, the spacer 120, can have alternative shapes such as circular, wedge, oval, ovoid, football-shaped, and rectangular-shaped with rounded corners and other shapes, and be within the spirit and scope of the invention. The shape of the spacer can be selected for a particular patient so that the physician can position the implant as close as possible to the anterior portion of the surface of the spinous process. The shape selected for the spacer 120 can effect the contact surface area of the implant 100 and the spinous processes that are to be subject to distraction. Increasing the contact surface area between the implant and the spinous processes can distribute the force and load between the spinous frame and the implant.

As can be seen in FIG. 2, the wing 130 in this embodiment 100 is elliptically-shaped in cross-section perpendicular to a longitudinal axis 125 of the spacer 120 and distraction guide 110. The dimensions of the wing 130 can be larger than that of the spacer 120, particularly along the axis of the spine, and can limit or block lateral displacement of the implant in the direction of insertion along the longitudinal axis 125. As illustrated in the embodiment of FIG. 3, the wing 130 can have other cross-sectional shapes, such as teardrop, wedge, circular, oval, ovoid, football-shaped, and rectangular-shaped with rounded corners and other shapes, and be within the spirit and scope of the invention. The wing 130 has an anterior portion 133 and a posterior portion 135.

In other embodiments, the implant 100 can have two wings, with a second wing 160 (shown in FIG. 4) separate from the distraction guide 110, spacer 120 and first wing 130. The second wing can be connected to the proximal end of the spacer 120. The second wing 160, similar to the first wing 130, can limit or block lateral displacement of the implant 100, however displacement is limited or blocked in the direction opposite insertion. When both the first wing 130 and second wing 160 are connected with the implant and the implant is positioned between adjacent spinous processes, a portion of the spinous processes can be sandwiched between the first and second wing, limiting any displacement along the longitudinal axis 125.

Figure 4:
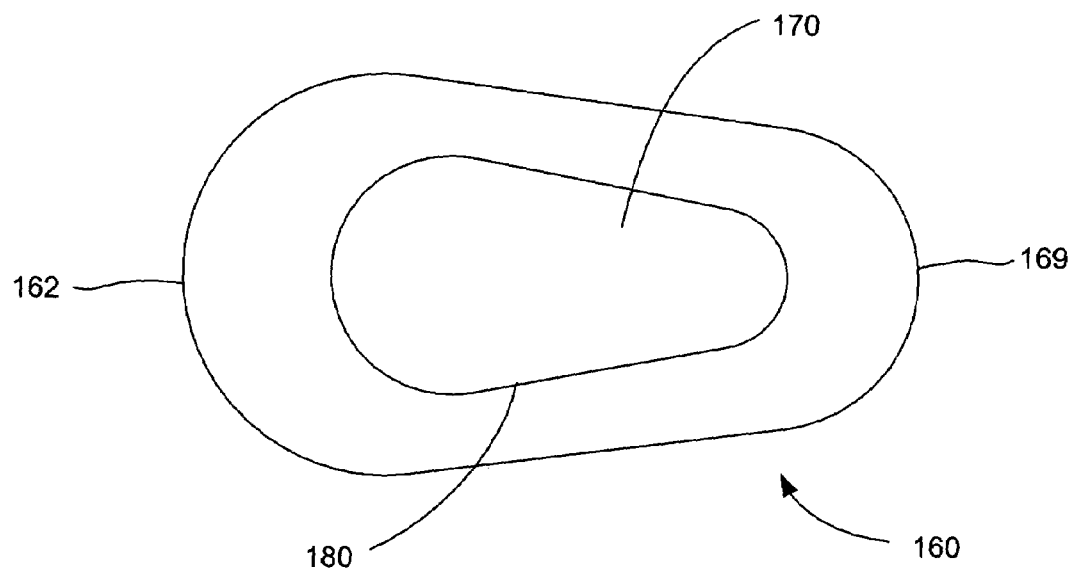
FIG. 4 is an end view of a second wing for use with the implant of FIG. 3.

As can be seen in FIG. 4, the second wing 160 can be teardrop-shaped in cross-section. The wider section or end 162 of the teardrop shape is the posterior end of the second wing 160 and the narrower section or end 169 is the anterior end of the second wing 160. Unlike the first wing 130, however, the sides of the second wing 160 define a space 170 with a lip 180 that allows the second wing 160 to pass over the distraction guide 110 to meet and connect with the spacer 120. The second wing 160 is then secured to the spacer 120 toward the end of the spacer located distally from the first wing 140. The second wing 160 is connected with the implant after the implant 100 is positioned between the spinous processes.

It is to be understood that the implant can be made in two pieces. The first piece can include the first wing 130, the spacer 120, and the distraction guide 110. The second piece can include the second wing 160. Each piece can be manufactured using technique known in the art (e.g., machining, molding, extrusion). Each piece, as will be more fully discussed below, can be made of a material that is bio-compatible with the body of the patient. For example the implants can be made of stainless steel and titanium. Additionally, a shape memory metal such as Nitinol, which is a combination of titanium and nickel, can also be used. Further polymers can also be used. The implant can be formed with multiple pieces and with the pieces appropriately joined together, or alternatively, the implant can be formed as one piece or joined together as one piece.

Figure 5:
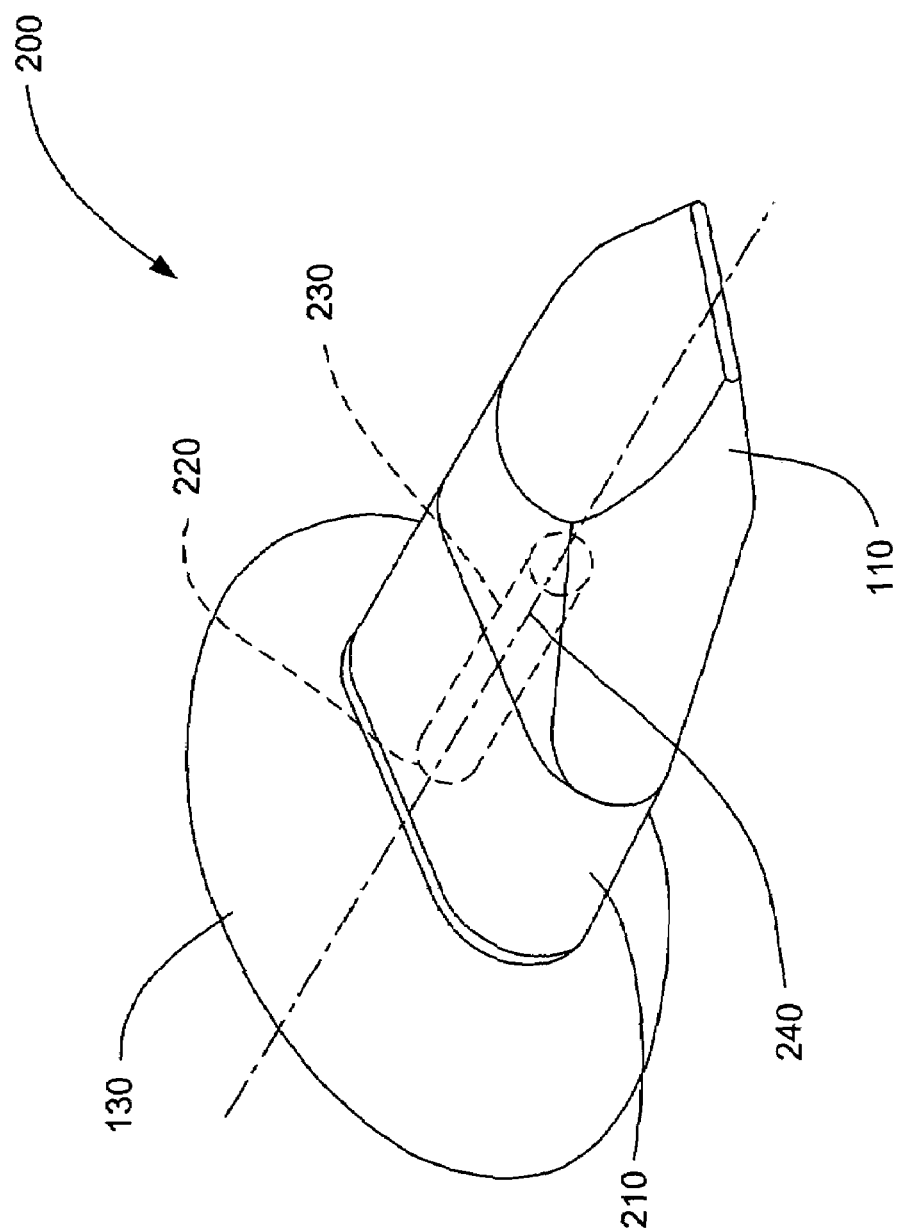
FIG. 5 is a perspective view of an embodiment of an implant in accordance with the present invention having a rotatable spacer and a wing with an elliptical cross-section.
Figure 6:
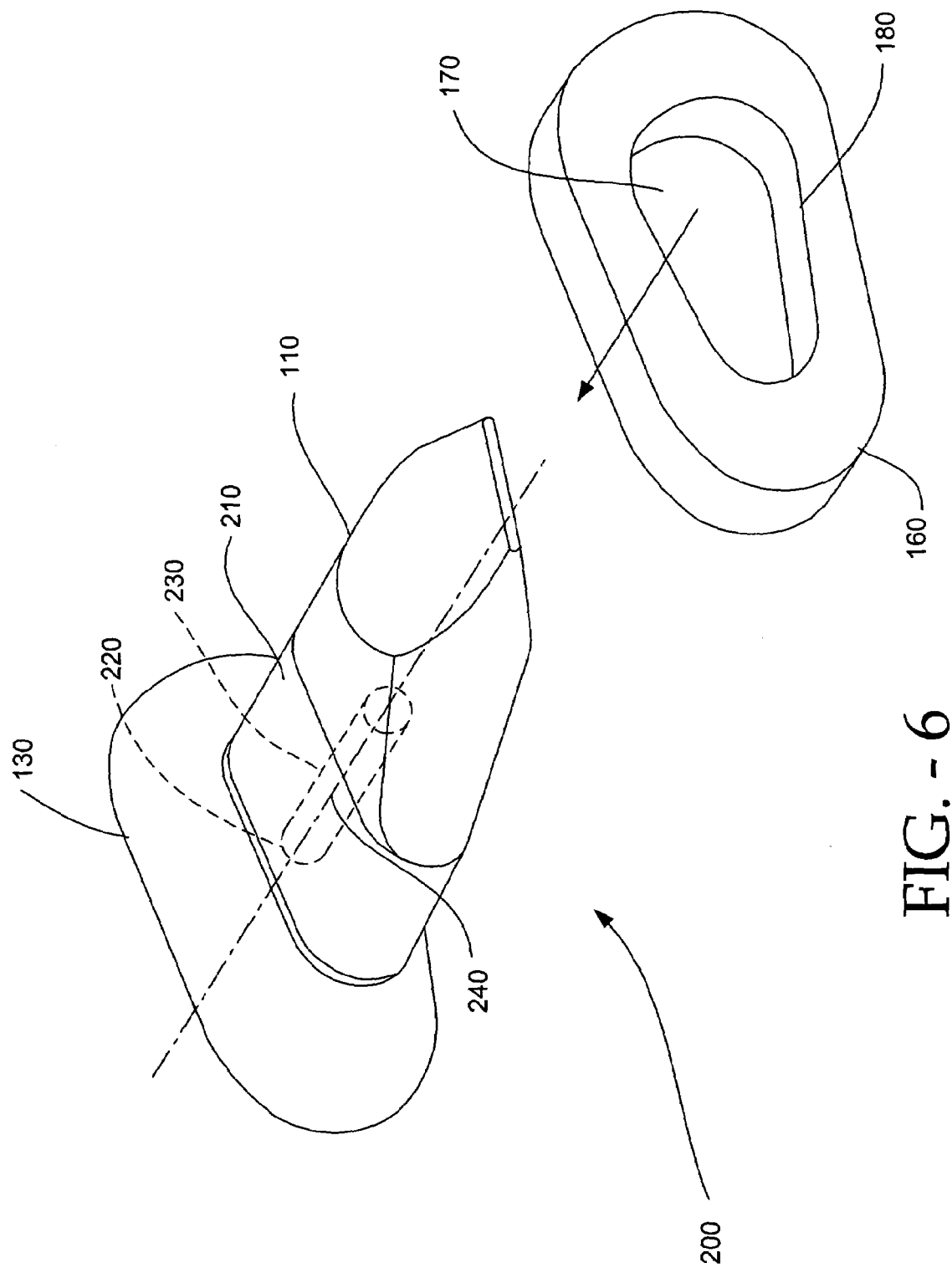
FIG. 6 is a perspective view of an embodiment of an implant in accordance with the present invention having a rotatable spacer with two wings that are teardrop-shaped in cross-section.
Figure 7:
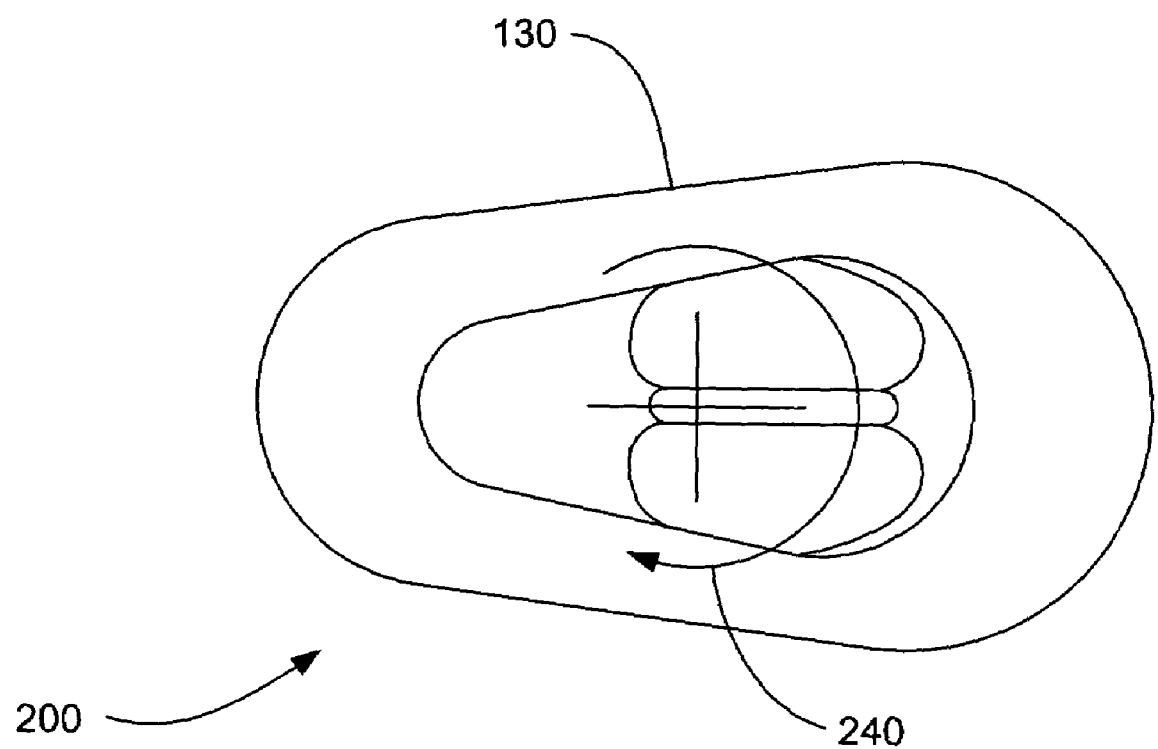
FIG. 7 depicts the axis of rotation of the implant of FIG. 6 as seen from an end view.

Further embodiments of implants in accordance with the present invention are depicted in FIGS. 5-7. In such embodiments, the spacer 210 can be rotatable about the longitudinal axis 240 relative to the first wing 130, or relative to a first and second wing 130,160 where two wings are used. The spacer 210 can be rotatable or fixed relative to the distraction guide 110. Where the spacer 210 is rotatable, the spacer 210 can include a bore 220 running the length of the longitudinal axis 240, and a shaft 230 inserted through the bore 220 and connecting the distraction guide 110 with the first wing 130. It can be advantageous to position any of the implants taught herein as close as possible to the vertebral bodies. The rotatable spacer 210 can rotate to conform to or settle between the bone structures of the cervical spine as the implant is inserted between the spinous processes, so that on average the contact surface area between the spacer 210 and both of the spinous processes can be increased over the contact surface area between a fixed spacer 210 and the spinous processes. Thus, the rotatable spacer 210 improves the positioning of the spacer independent of the wings relative to the spinous processes. The embodiment of FIG. 6 has a first wing 130 and if desired, a second wing 160 similar to the wing depicted in the embodiment of FIG. 3. As discussed below, the shape of the wings in FIGS. 3 and 6 is such that the implants accommodate the twisting of the cervical spine along its axis as, for example, the head of a patient turning from side to side.

Figure 8:
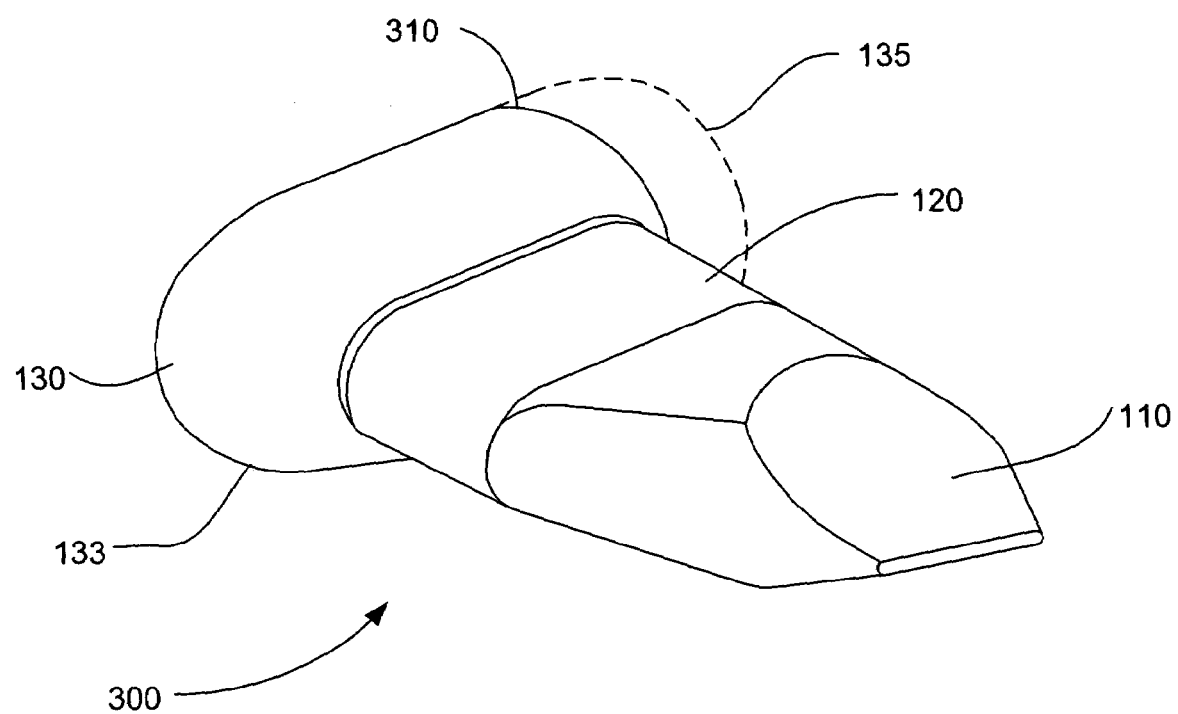
FIG. 8 is a perspective view of an embodiment of an implant in accordance with the present invention having a wing that is truncated at a posterior end.
Figure 9A:
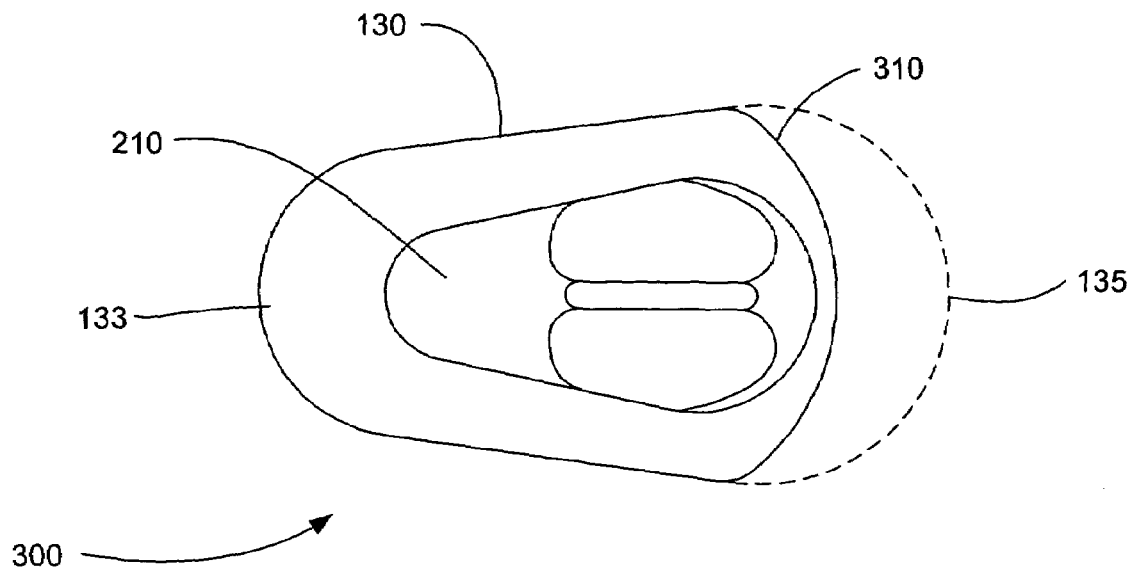
FIG. 9A is an end view of an embodiment of an implant in accordance the present invention having a wing truncated at a posterior end and a rotatable spacer.
Figure 9B:
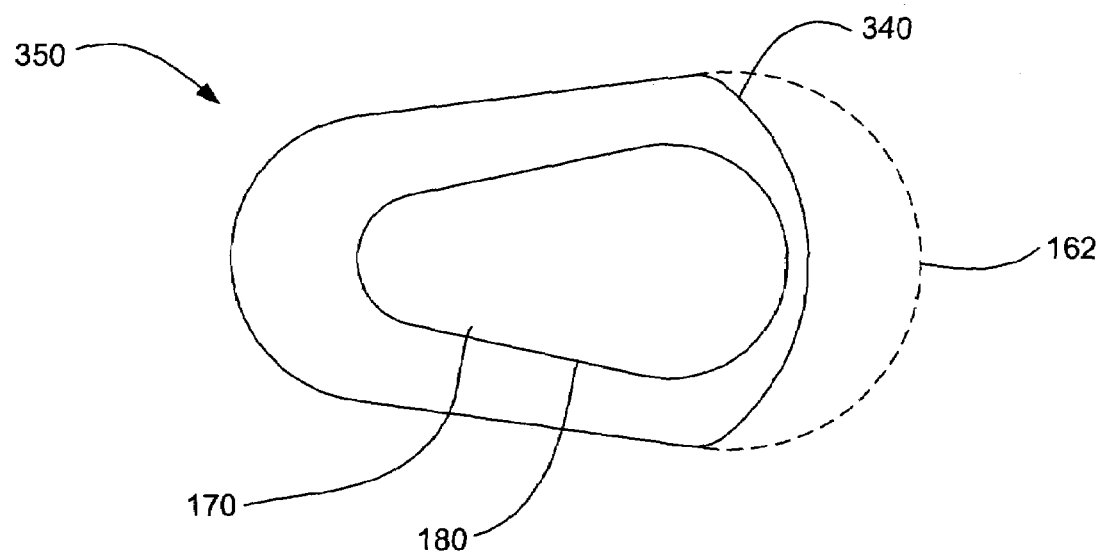
FIG. 9B is a truncated second wing for use with the implant of FIG. 9A.

FIG. 8 is a perspective view and FIG. 9A is an end view of still another embodiment of an implant in accordance with the present invention, wherein the posterior portion 135 of the teardrop-shaped first wing 130 is truncated 310, making the first wing 130 more ovoid in shape. In this configuration, the anterior portion 133 of the first wing 130 can be longer than the truncated posterior end 310 of the first wing 130. As in previous embodiments, the spacer 210 of such implants 300 can be a rotatable spacer rather than a fixed spacer. FIG. 9B illustrates a second wing for use with such implant 300 having a truncated posterior end 340. Truncation of the posterior ends 310,340 of the first and second wings 130,160 can reduce the possibility of interference of implants 300 having such first and second wings 130,160 positioned between spinous processes of adjacent pairs of cervical vertebrae, e.g., implants between cervical vertebrae five and six, and between six and seven. During rotation of the neck, the spinous process move past each other in a scissor-like motion. Each cervical vertebra can rotate relative to the next adjacent cervical vertebra in the general range of about 6°-12°. In addition, about 50 percent of the rotational movement of the neck is accomplished by the top two neck vertebrae. Thus, such embodiments can accommodate neck rotation without adjacent embodiments interfering with each other.

Figure 10:
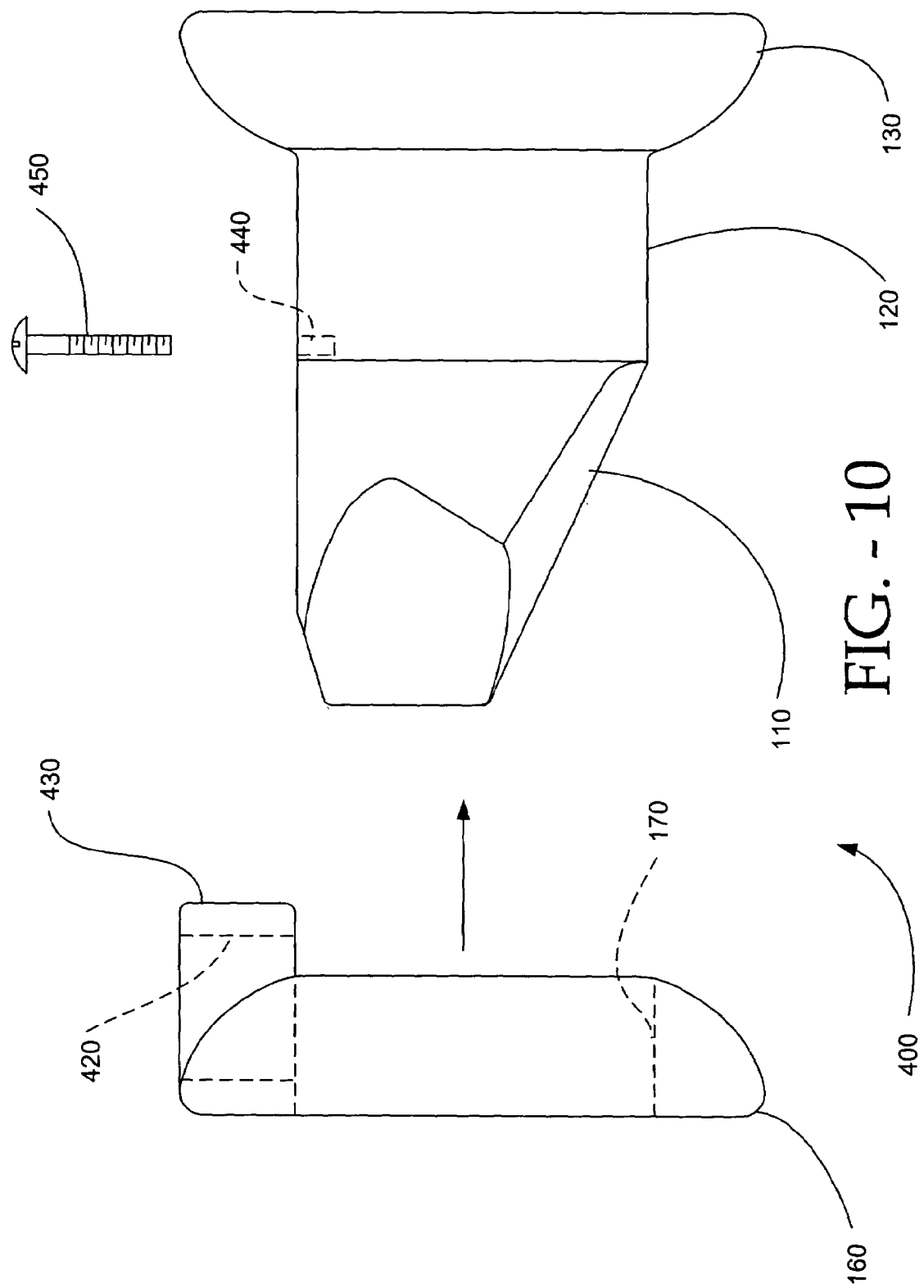
FIG. 10 is a plan view of an embodiment of an implant in accordance with the present invention wherein a screw is used to secure a second wing to the spacer.
Figure 11:
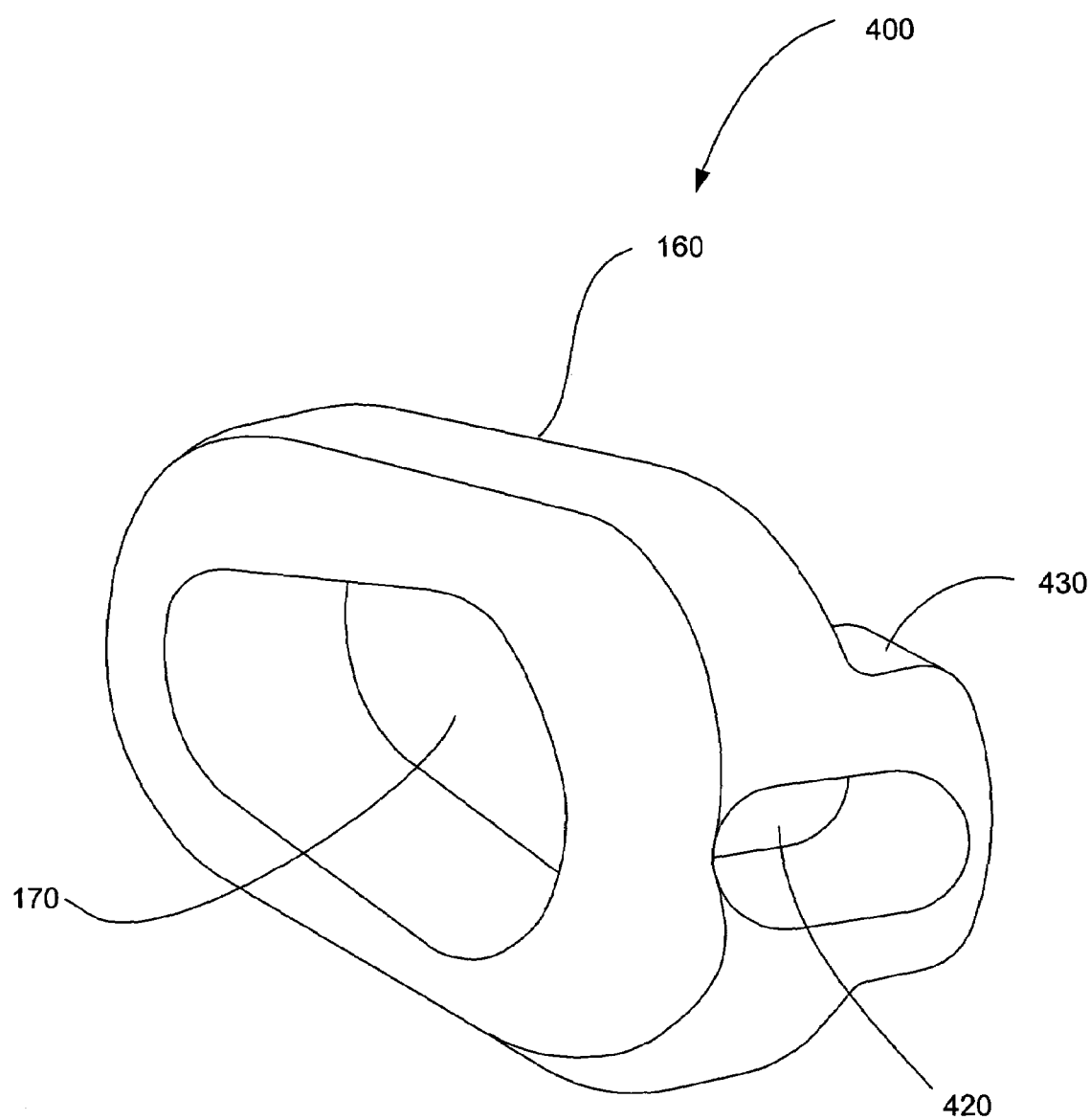
FIG. 11 is a perspective view of the second wing of FIG. 10.
Figure 12:
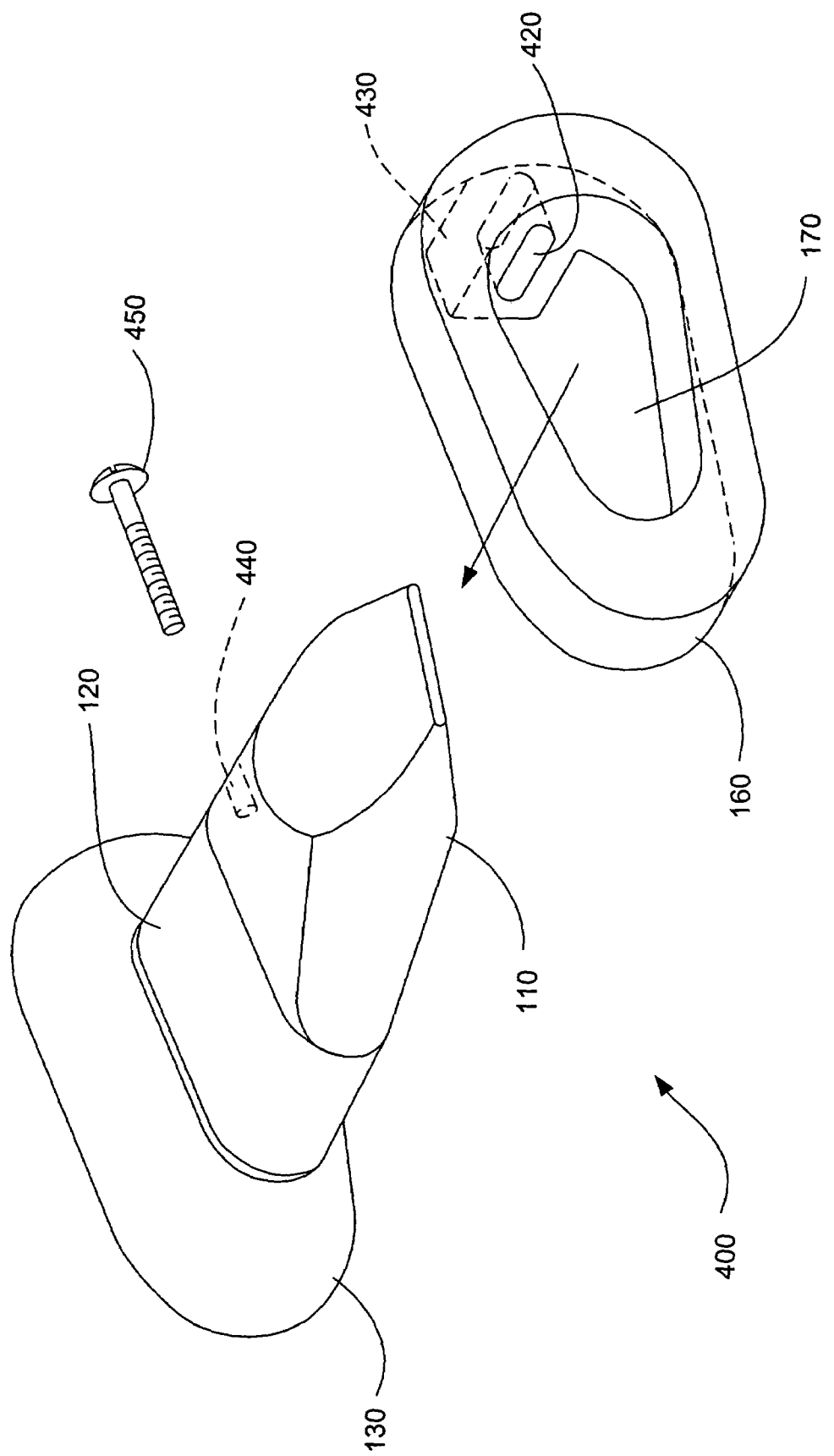
FIG. 12 is a perspective view of the implant of FIG. 10.
Figure 13A:
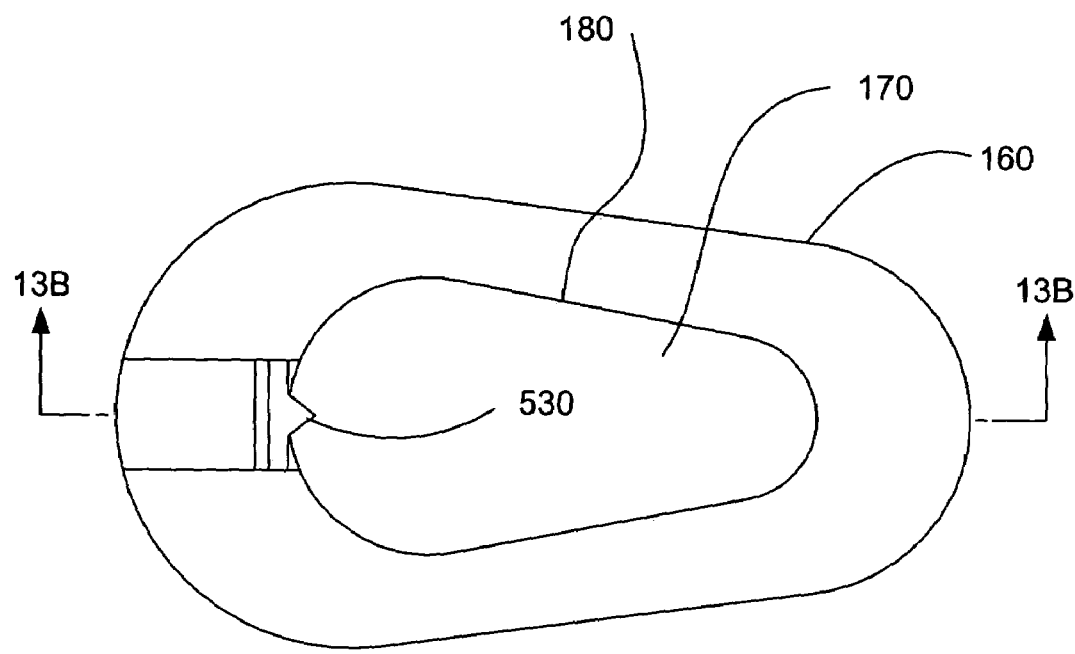
FIG. 13A is a front view of a second wing for use with some embodiments of implants of the present invention having a flexible hinge mechanism for securing the second wing to an implant.
Figure 13B:
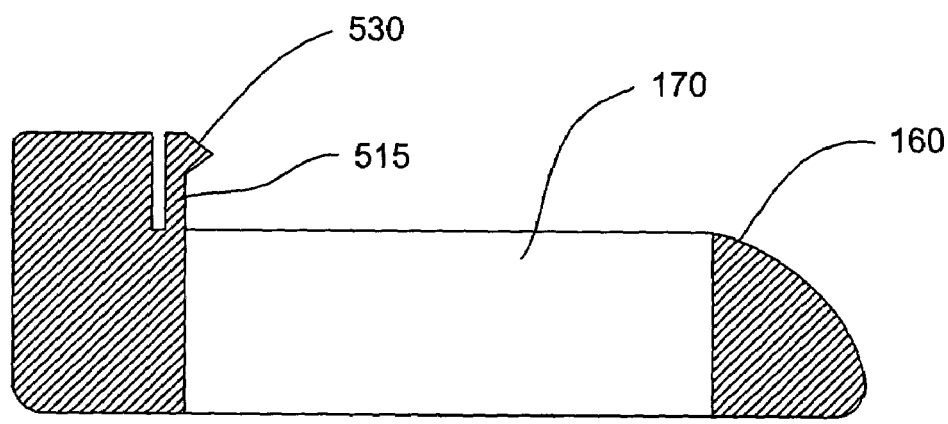
FIG. 13B is a side-sectional view of the second wing of FIG. 13A.
Figure 14A:
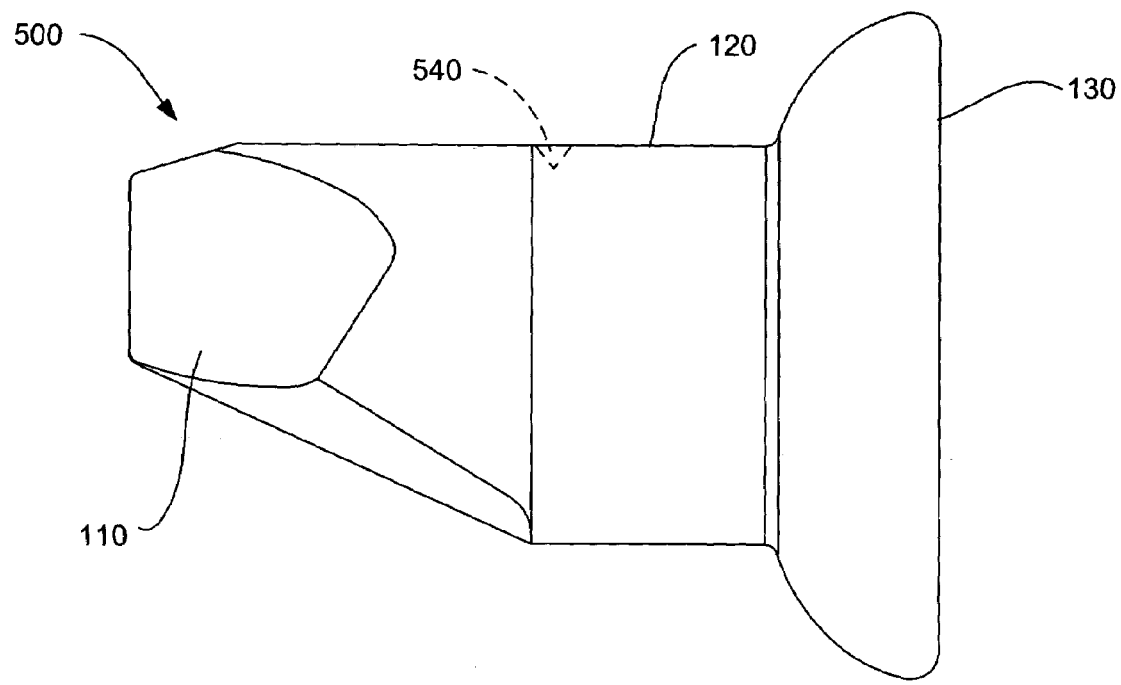
FIG. 14A is a plan view of an embodiment of an implant for use with the second wing of FIGS. 13A and 13B.
Figure 14B:
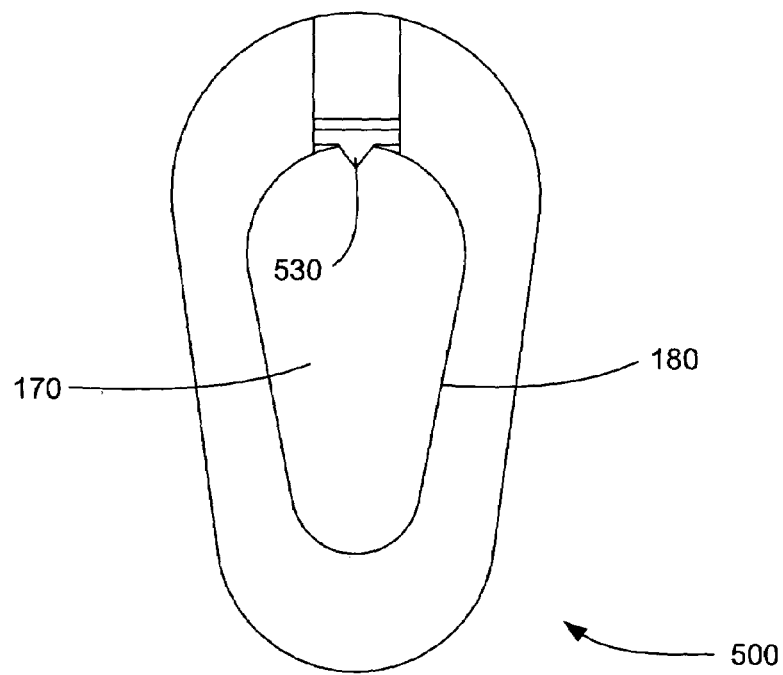
FIG. 14B is a front view of the second wing of FIGS. 13A and 13B.

With respect to the prior embodiments which have first and second wings, the second wing 160, can be designed to be interference-fit onto the spacer 120 (where the spacer is fixed) or a portion of the distraction guide 110 adjacent to the spacer 120 (where the spacer is rotatable). Where the second wing 160 is interference-fit, there is no additional attachment device to fasten the second wing 160 relative to the remainder of the implant. Alternatively, various fasteners can be used to secure the second wing 160 relative to the remainder of the implant. For example, FIGS. 10-12 illustrate an embodiment of an implant 400 including a teardrop-shaped second wing 410 having a bore 420 through a tongue 430 at the posterior end of the second wing 160. The bore on the second wing 420 is brought into alignment with a corresponding bore 440 on the spacer 120 when the second wing 160 is brought into position by surgical insertion relative to the rest of the implant. A threaded screw 450 can be inserted through the aligned bores in a posterior-anterior direction to secure the second wing 160 to the spacer 120. The direction of insertion from a posterior to an anterior direction has the screw engaging the bores and the rest of the implant along a direction that is generally perpendicular to the longitudinal axis 125. This orientation is most convenient when the surgeon is required to use a screw 450 to secure the second wing 160 to the rest of the implant. Other securing mechanisms using a member inserted into corresponding bores 420,440 on the spacer 120 and second wing 160 are within the spirit of the invention. It should be understood that a rotatable spacer 210 also can be accommodated by this embodiment. With a rotatable spacer 210, the second wing 160 would be attached to a portion of the distraction guide 110 that is located adjacent to the rotatable spacer 210.

FIGS. 13A-14B depict a further embodiment 500 wherein the second wing 160 is secured to the spacer 120 by a mechanism including a flexible hinge 515, with a protrusion 530 on the end of the hinge 510 adjacent to the lip 180 of the hole 170 defined by portions of the second wing 160. The securing mechanism also encompasses an indentation 540 on the spacer 120, wherein the indentation accommodates the protrusion 530 on the end of the flexible hinge 515. During surgery, after insertion of the distraction guide 110, spacer 120, and first wing 130, the second wing 160 is received over the distraction guide 110 and the spacer 120. As the second wing 160 is received by the spacer 120, the flexible hinge 515 and its protrusion 530 deflect until the protrusion 530 meets and joins with the indentation 540 in the spacer 120, securing the second wing 160 to the spacer 120. Again in embodiments where the spacer can rotate, the indentation 540 is located on an end of the distraction guide 110 that is adjacent to 150 the rotatable spacer 210. With respect to the flexible hinge 515, this hinge is in a preferred embodiment formed with the second wing 160 and designed in such a way that it can flex as the hinge 515 is urged over the distraction guide 110 and the spacer 120 and then allow the protrusion 530 to be deposited into the indentation 540. Alternatively, it can be appreciated that the indentation 540 can exist in the second wing 160 and the flexible hinge 515 and the protrusion 530 can exist on the spacer 120 in order to mate the second wing 160 to the spacer 120. Still alternatively, the flexible hinge 515 can be replaced with a flexible protrusion that can be flexed into engagement with the indentation 540 in the embodiment with the indentation 540 in the spacer 120 or in the embodiment with the indentation 540 in the second wing 160.

Figure 15A:
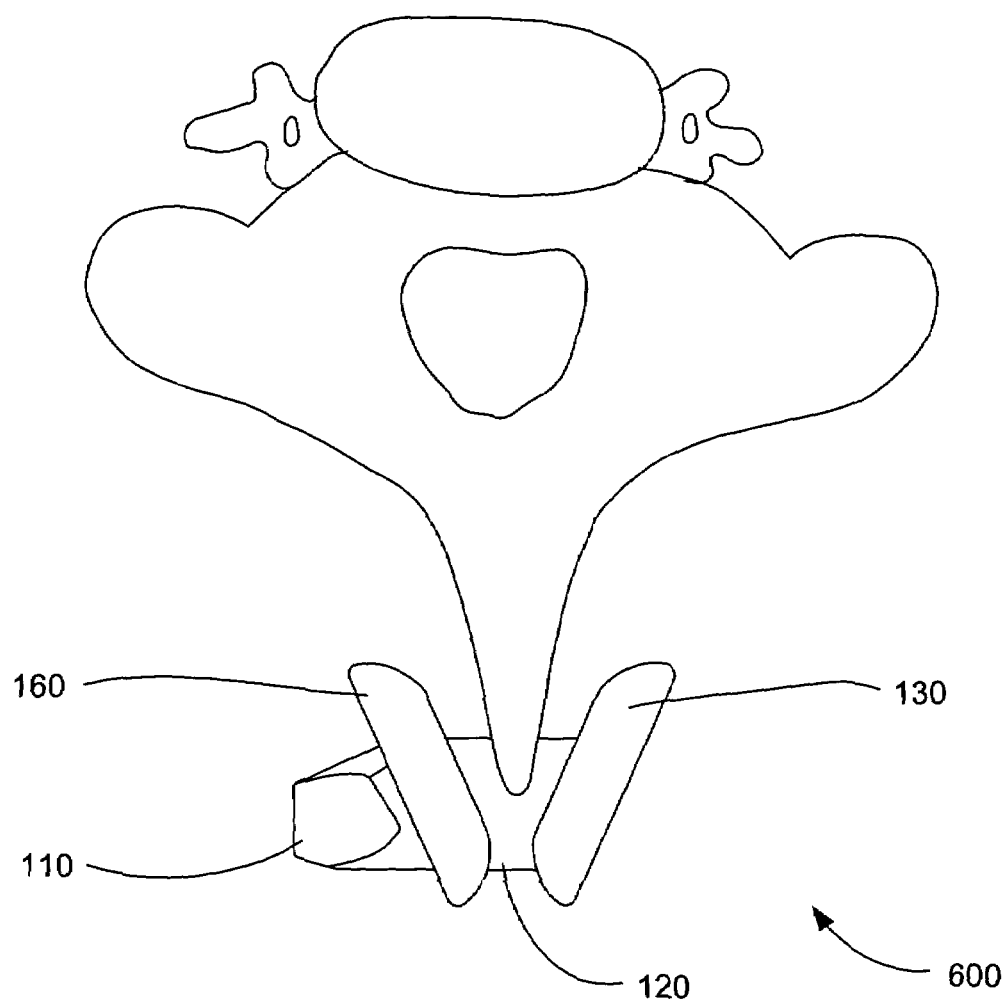
FIG. 15A is a top view of an embodiment of an implant in accordance with the present invention positioned between the spinous processes of adjacent cervical vertebrae.
Figure 15B:
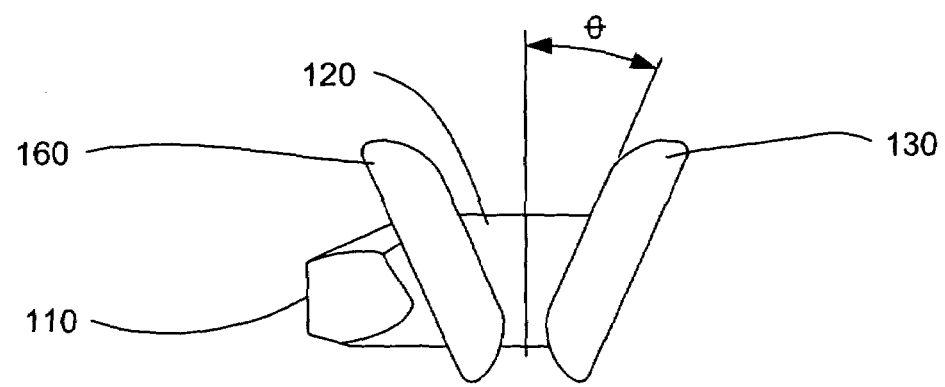
FIG. 15B is a top view of the implant of FIG. 15A.
Figure 16:
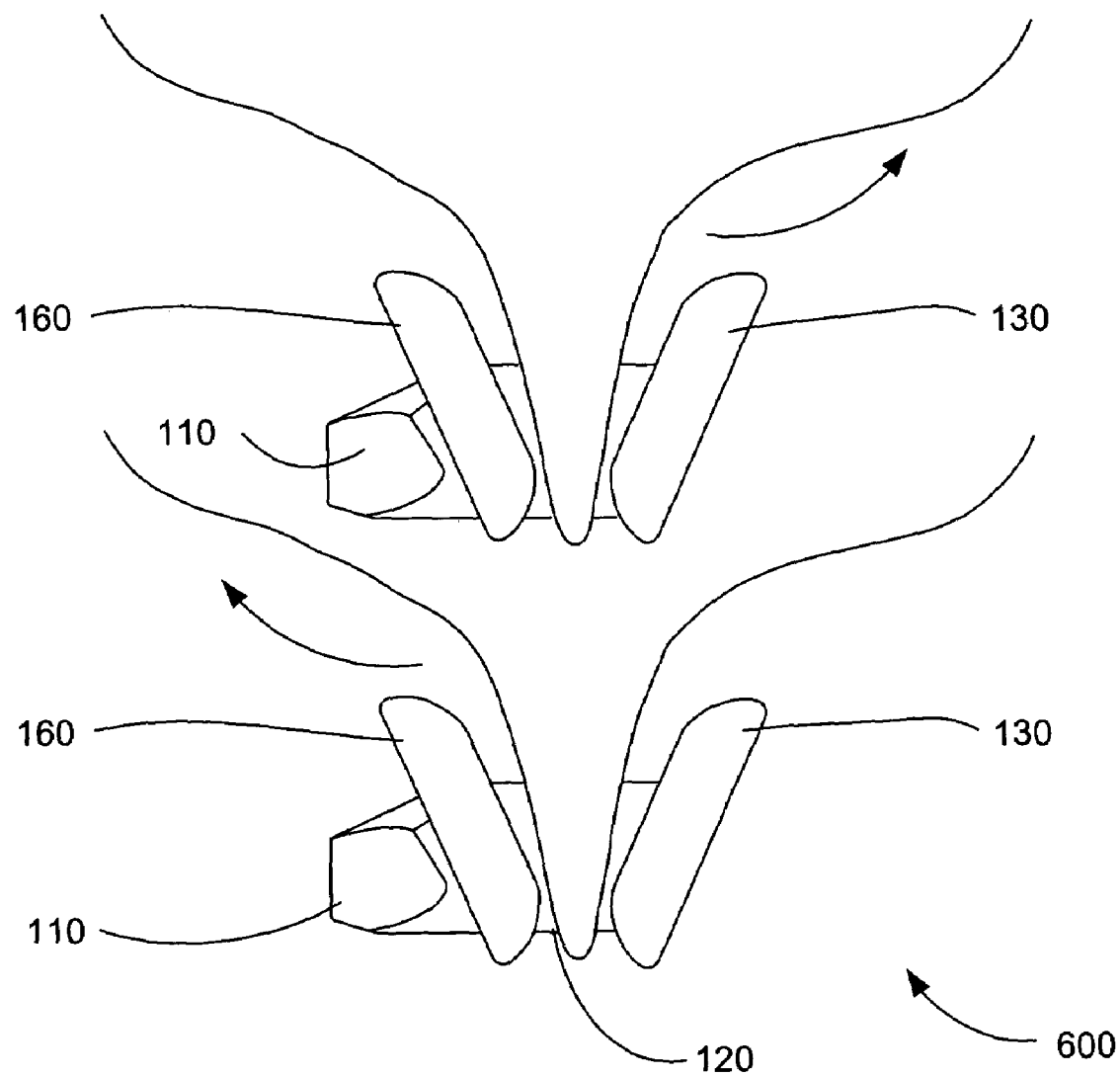
FIG. 16 is a top view of two such implants of the invention as seen in FIG. 15, positioned in the cervical spine.

FIGS. 15A-16 illustrate an embodiment of an implant 600 wherein anterior ends of a first wing 130 and second wing 160 flare out at an angle away from the spacer 120 and away from each other. The cervical spinous processes are themselves wedge-shaped when seen from a top view. That the implant 600 can roughly conform with the wedge shape so that the implant 600 can be positioned as close as possible to the vertebral bodies of the spine where the load of the spine is carried. Thus the first 130 and the second wings 160 are positioned relative to the spacer, whether the spacer is fixed 120 or rotatable 210, so that the wings flare out as the wings approach the vertebral body of the spine. FIG. 15B depicts a top view of the implant 600 of FIG. 15A. As is evident from FIG. 15B, the first wing 130 is aligned at an angle with respect to a line perpendicular to the longitudinal axis. In one embodiment, the angle is about 30°, however, the angle θ can range from about 15° to about 45°. In other embodiments, other angles of the first wing 130 relative to the spacer 120 outside of this range are contemplated and in accordance with the invention. Likewise, the second wing 160 can be aligned along a similar, but oppositely varying range of angles relative to the line perpendicular to the longitudinal axis. The first and second wing 130,160 thus form an obtuse angle with respect to the spacer 120 in this embodiment. The second wing 160 defines an inner hole 170 which is outlined by the lip 180. As is evident, the lip 180 can be provided at an angle relative to the rest of the second wing 160 so that when the lip 180 is urged into contact with the spacer 120, the second wing 160 has the desired angle relative to the spacer 120. As discussed above, there are various ways that the second wing 160 is secured to the spacer 120. FIG. 15A depicts a top view of one such implant 600 placed between the spinous processes of adjacent cervical vertebrae. FIG. 16 is a top view illustrating two layers of distracting implants 600 with flared wings.

Figure 17:
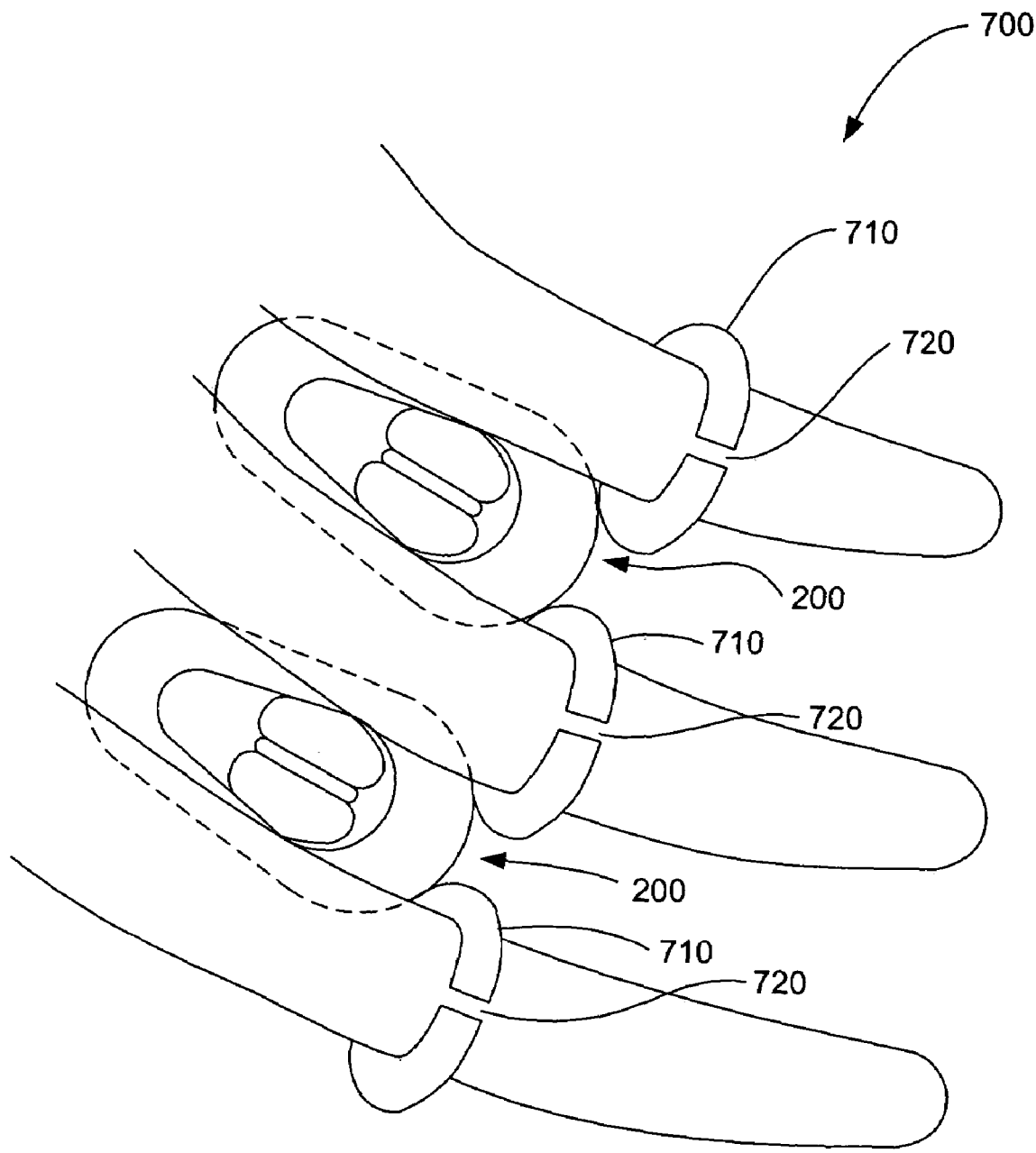
FIG. 17 is a side view of two implants of the invention positioned in the cervical spine, with stops or keeps at the distal ends of the spinous processes.

Systems and methods in accordance with the present invention can include devices that can be used in cooperation with implants of the present invention. FIG. 17 illustrates "stops" (also referred to herein as "keeps") 710, which are rings of flexible biocompatible material, which can be positioned around the spinous processes of adjacent cervical vertebrae and located posteriorly to the implant. The keeps 710 can prevent posterior displacement of the implants. In one embodiment, the keeps can include a ring 710 having a slit 720. The keeps 710 can be somewhat sprung apart, so that the keep 710 can be fit over the end of the spinous process and then allowed to spring back together in order to hold a position on the spinous process. The keep 710 can act as a block to the spacer 120 in order to prevent the implant from movement in a posterior direction.

Distractible Interspinous Implants

Figure 18:
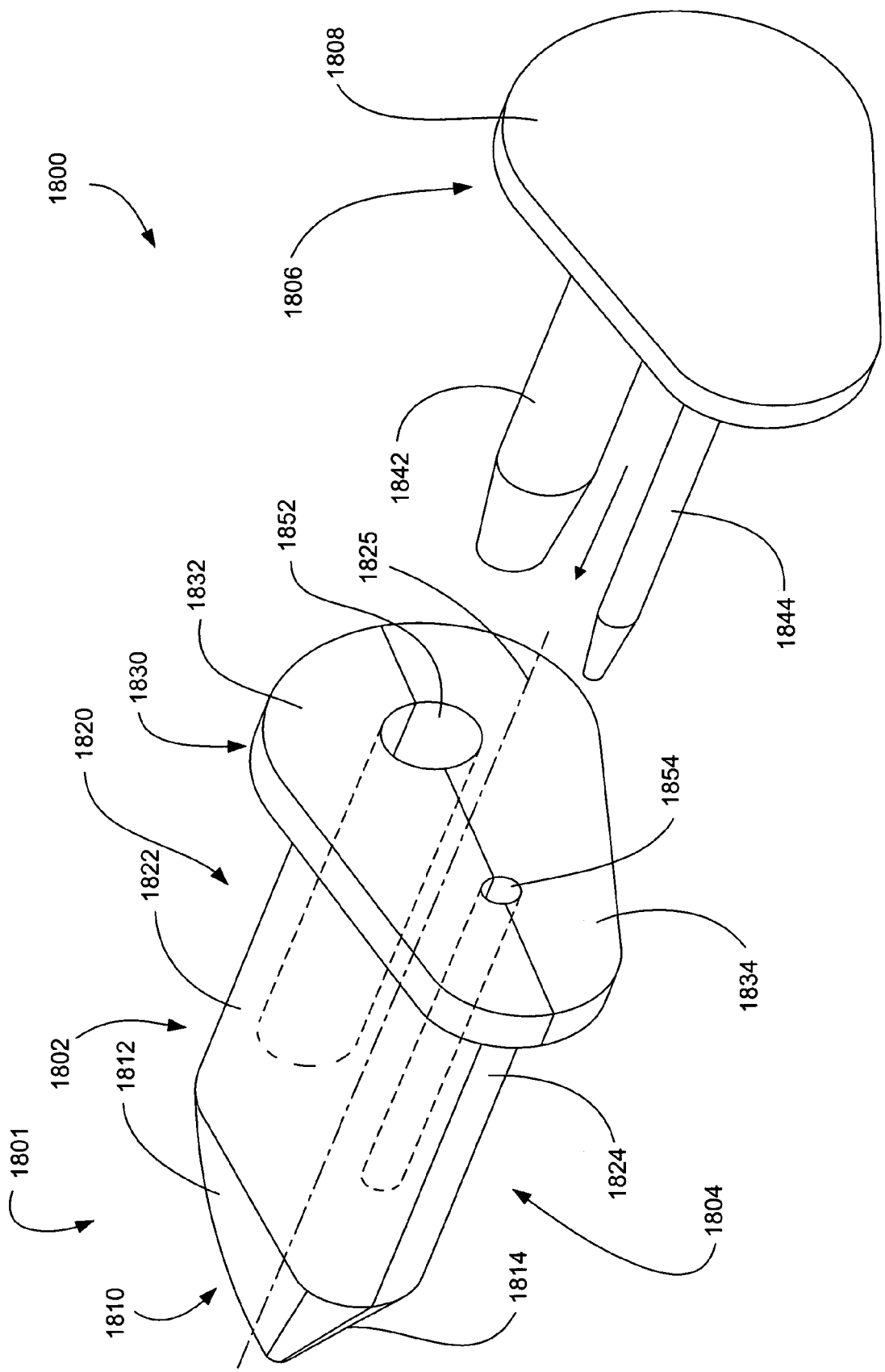
FIG. 18 is a perspective view of an alternative embodiment of an implant for use with systems and methods of the present invention.
Figure 19A:
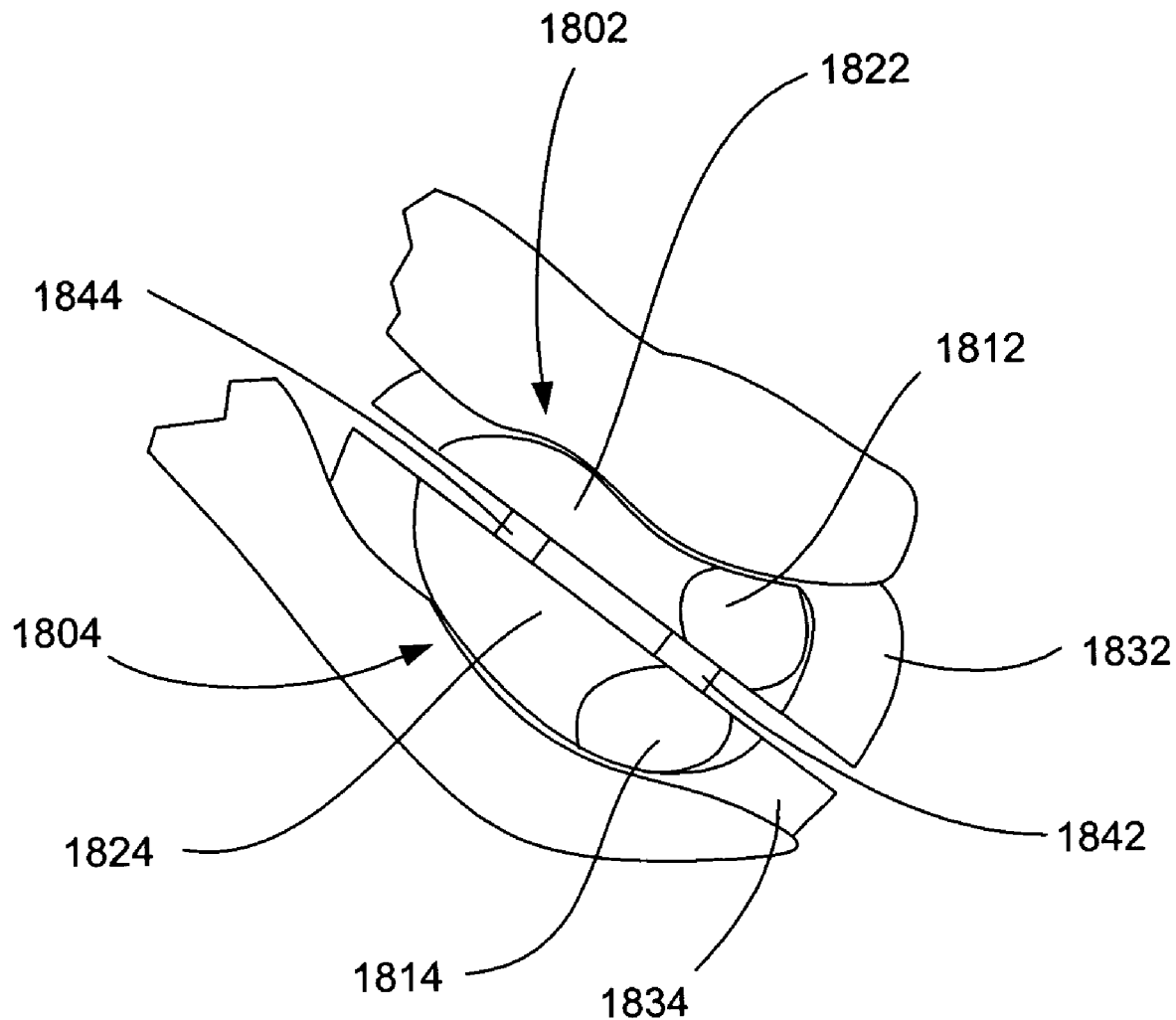
FIG. 19A is an end view of an implant in accordance with still another embodiment of the present invention having a first part shaped to conform roughly with a contact surface of the spinous process.

In still other embodiments, implants in accordance with the present invention can be distractible in situ. FIG. 18 is a perspective view of one such implant. The implant 1800 comprises a body 1801 adapted to be inserted between the spinous processes, and a distracting insert 1806. The body 1801 can include two substantially mirror parts: a first part 1802 adapted to contact and support an upper spinous process and a second part 1804 adapted to contact and support a lower spinous process. When positioned such that the first and second parts 1802,1804 align with and abut one another, the body 1801 can resemble implants described above in reference to FIGS. 1-17. In other embodiments, the body 1801 can have a shape other than those shown in FIGS. 1-17. Further, in some embodiments the first part 1802 and second part 1804 can have different shapes, such that when the first part 1802 and second part 1804 align with and abut one another, the body 1801 is nonsymmetrical about the plane of contact. For example, as shown in FIG. 19A, the first part 1802 can have a saddle-like, or concave shape conforming roughly with a shape of a contact surface of the second cervical, while the second part 1804 has a substantially convex shape.

The body 1801 can include a wing 1830 having a first and second portion 1832,1834, a spacer 1820 having a first and second portion 1822,1824, and a lead-in tissue expander (also referred to herein as a distraction guide) 1810 having a first and second portion 1812,1814. The distraction guide 1810 as shown is wedge-shaped, i.e., the distraction guide 1810 has an expanding cross-section from the proximal end of the body 1801 to a region where the distraction guide 1810 joins with the spacer 1820. As such, the distraction guide 1810 functions to initiate distraction of the soft tissue and the spinous processes when the body 1801 is surgically inserted between the spinous processes.

The spacer 1820, as shown, is teardrop-shaped in a cross-section perpendicular to the spacer's longitudinal axis 1825. The spacer 1820 can be shaped to roughly conform to a wedge-like space, or a portion of the space, between adjacent spinous processes, for example as between the spinous processes of the fourth and fifth cervical vertebrae. The shape of the spacer 1820 can be selected for a particular patient, and/or a particular pair of adjacent spinous processes, and can vary substantially. Thus, in other embodiments, the spacer 1820 can have other cross-sectional shapes, such as circular, wedge, oval, ovoid, football-shaped, and rectangular-shaped with rounded corners and other cross-sectional shapes and/or can be custom fabricated for the particular patient and the anatomy of the particular spinal processes between which the implant 1800 is to be placed. In still other embodiments, the spacer 1820 can have a nonsymmetrical cross-sectional shape, for example where a space between adjacent spinous processes is nonsymmetrical. The ability to select a size and shape of the spacer 1820 to suit a patient allows the physician to choose an implant 1800 that can be placed closer to the vertebral bodies than farther away for additional support. The shape selected for the spacer 1820 can define the contact surface area between the implant 1800 and the spinous processes that are subject to distraction. Increasing the contact surface area between the implant 1800 and the spinous processes distributes the force and load between the spinous frame and the implant 1800. Generally, a teardrop or wedge-shaped spacer 1820 can allow for more load-bearing contact between the spacer 1820 and the spinous processes of the cervical vertebrae, and embodiments having such shapes will be more particularly described.

As shown, the wing 1830 can be tear-drop shaped in cross-section, although having a minor dimension that is larger than that of the spacer 1820, and can limit or block lateral displacement of the implant 1800 in the direction of insertion along the longitudinal axis 1825. However, the wing 1830 need not be teardrop shaped. In other embodiments, the wing 1830 can have some other shape, for example the wing 1830 can be elliptical, wedge, circular, oval, ovoid, football-shaped, and rectangular-shaped with rounded corners and other shapes, and be within the spirit and scope of the invention. Further, as with the spacer 1820, the wing 1830 can have a nonsymmetrical cross-sectional shape. The shape of the wing 1830 can be chosen to most easily fit into place while avoiding obstructions, such as soft tissue or bone, or other implants, while still blocking or limiting lateral displacement.

Figure 19B:
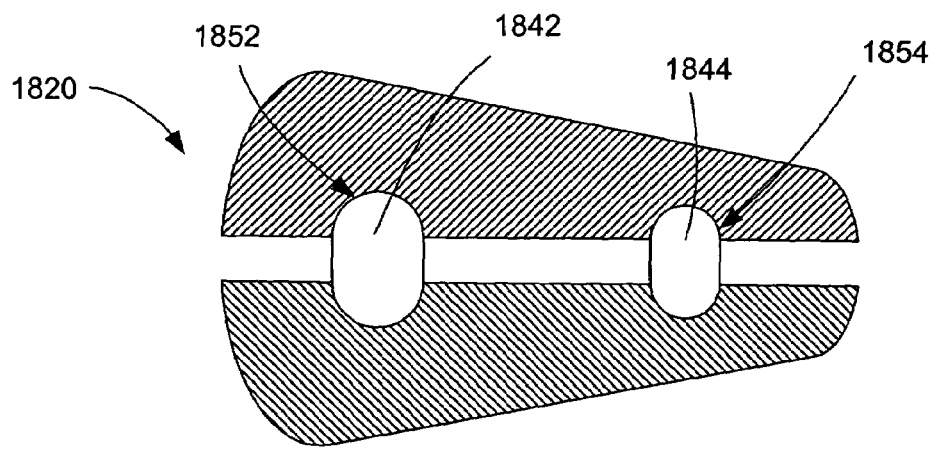
FIG. 19B is a cross-sectional view of a spacer and a distracting insert in accordance with one embodiment of the present invention.
Figure 19C:
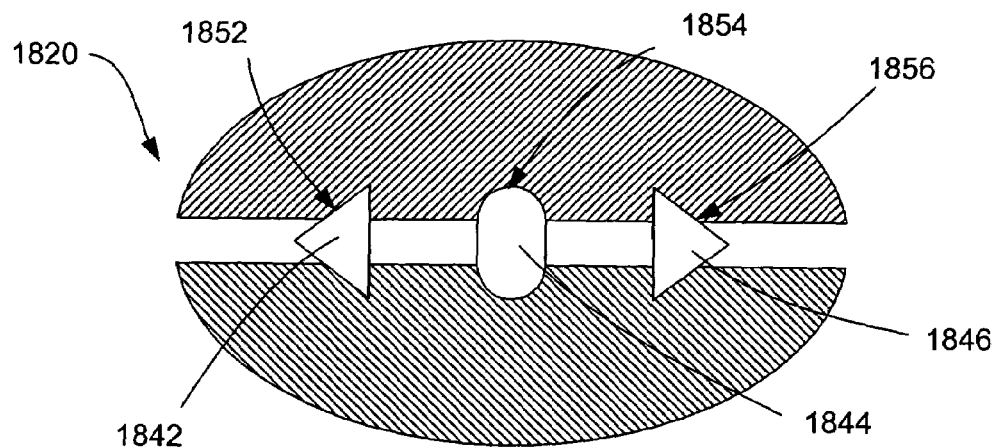
FIG. 19C is a cross-sectional view of a spacer and a distracting insert in accordance with an alternative embodiment of the present invention.
Figure 19D:
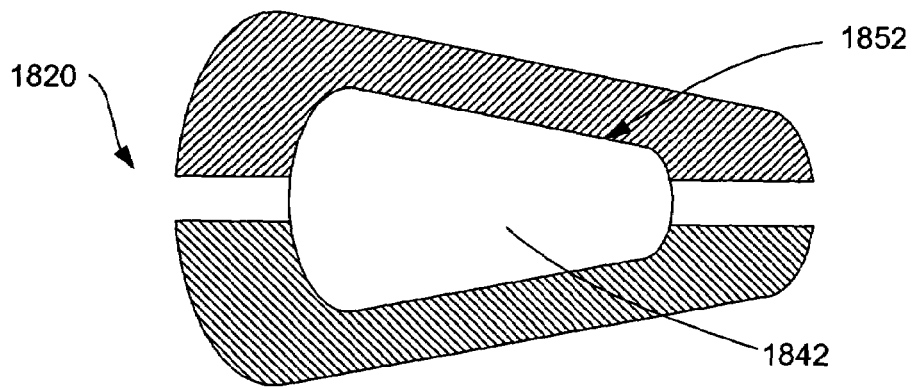
FIG. 19D is a cross-sectional view of a spacer and a distracting insert in accordance with still another embodiment of the present invention.

The wing 1830 can include one or more cavities 1852,1854 that extend through the wing 1830 and through at least a portion of the spacer 1820. The one or more cavities 1852, 1854 should comprise a first groove formed in the first part 1802 and a second groove formed in the second part 1804, so that the cross-section of the cavity 1852,1854 can be expanded during insertion of a distracting insert 1806, as described below. The body 1801 of FIG. 18 includes a first cavity 1852 and a second cavity 1854 to receive a first insert 1842 and a second insert 1844 of the distracting insert 1806. Having two or more cavities and corresponding inserts can prevent relative rotation between the body 1801 and the distracting insert 1806. In the embodiment shown in cross-section in FIG. 19B, each cavity has a substantially circular cross-section, and is sized roughly in proportion to the width of the spacer 1820, so that the first cavity 1852 is larger in diameter than the second cavity 1854. However, in other embodiments, the cavities need not be shaped as shown. For example, the cavities can be elliptical, dual-lobed, or otherwise shaped. Further, the cavities need not be sized as shown. For example, the cavities can be roughly the same size. As shown in FIG. 19C, in still further embodiments, the body 1801 can include more than two cavities 1852,1854,1856, and each cavity can have similar, or different shape. As shown in FIG. 19D, in still other embodiments the body 1801 can include a single cavity 1852, such as a wedge-shaped cavity roughly corresponding to a shape of the spacer 1820. Myriad different cavity shapes and cavity configurations can be employed to achieve separation of a body 1801 positioned between spinous processes. However, it can be preferable that the shape of the cavities 1852,1854,1856 should correspond roughly with the shape of the upper and lower surfaces of the inserts 1842,1844,1846 of the distracting insert 1806, so that, as shown in FIG. 19B-19D, a load applied to the body 1801 can be distributed relatively evenly over the surface of the cavities 1852,1854,1856.

Once the body 1801 is positioned between adjacent spinous processes, the first and second parts 1802,1804 of the body 1801 can be separated, thereby expanding the width of the body 1801 and distracting the adjacent spinous processes. In one embodiment, separation of the first and second parts 1802,1804 can be accomplished, for example, by positioning the distracting insert 806 within the body 1801 such that the first and second parts 1802,1804 are urged apart. As mentioned above, the distracting insert 1806 can include one or more inserts associated with the one or more cavities, the one or more inserts being fixedly connected to a cap 1808. As shown in FIG. 18, the distracting insert 1806 includes a first insert 1842 and a second insert 1844, each of the inserts being fixedly connected with a cap 1808 having a shape roughly corresponding to a shape of the wing 1830. Inserts 1842, 1844 have distracting tips that can initially urge the halves of the implant 1800 apart. In other words, the inserts 1842,1844 have tips with ever-increasing cross-section so that the tips can be easily inserted in the cavities 1852,1854 and the continual movement of the insert 1842,1844 urges the halves of the body 1801 apart. Thus, the tips of the insert 1842,1844 can be smaller than the cavities 1852,1854 in order to facilitate initial insertion into the cavities 1852,1854. As shown in FIG. 19B-D, the one or more inserts 1842,1844,1846 can be sized such that they have a height larger than a diameter (or height) of the one or more cavities 1852,1854,1856, so that when positioning the inserts within the cavities, the first part 1802 and second part 1804 of the body 1801 are separated by the difference in height of the inserts and the diameter (or height) of the cavities—i.e., an additional distraction height.

Figure 20A:
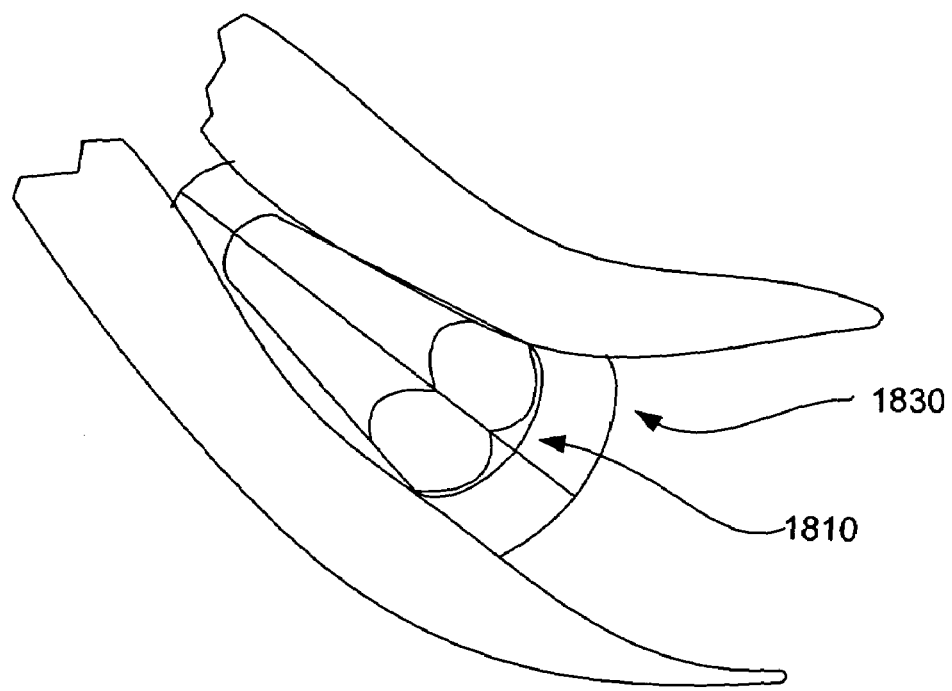
FIG. 20A is a front view of the implant of FIG. 18 inserted between spinous processes.
Figure 20B:
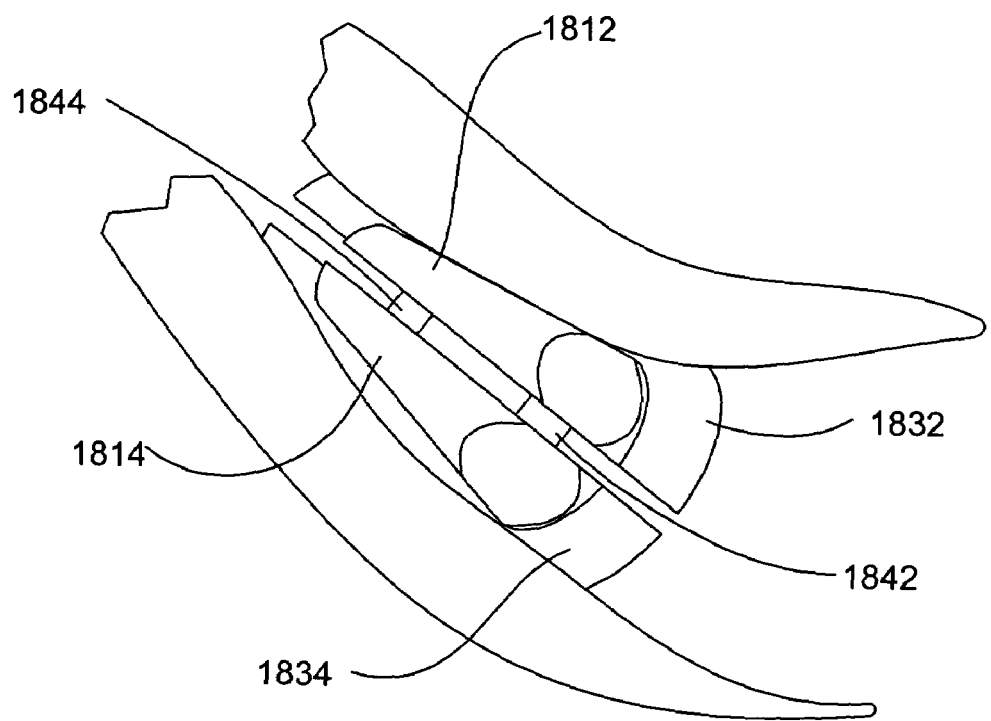
FIG. 20B is a front view of the implant of FIG. 20A having a distracting insert positioned within cavities of the implant.

As shown in FIG. 20A, the body 1801 can be inserted between adjacent spinous processes by piercing and/or displacing the soft tissue (i.e., the interspinous ligament) with the distraction guide 1810 and stretching and/or displacing the tissue so that the spacer 1820 fits between the spinous processes. The height of the first part 1802 and second part 1804 of the body 1801 can be minimized by abutting the first part 1802 and the second part 1804 so that the body 1801 can be positioned between the spinous processes. As described above, and as can be seen in FIG. 20A, the shape of the body 1801 can resemble the shape of a space between adjacent spinous processes. With the body 1801 in place, the distracting insert 1806 can be inserted into the body 1801, causing the first part 1802 and second part 1804 to separate, as described above and shown in FIG. 20B. As discussed above, proximal ends of the inserts 1842,1844 of the distracting insert 1806 can be tapered to assist in guiding the inserts 1842,1844 into the cavities 1852,1854, and to ease separation of the first and second parts 1802,1804. The distracting insert 1806 can have inserts 1842,1844 sized to achieve a desired amount of distraction of the spinous processes.

As with the body 1801, multiple distracting inserts 1806 can be made available to a physician, the physician choosing a distracting insert 1806 sized to suit a particular patient. A system in accordance with one embodiment of the present invention can comprise a plurality of bodies 1801, each body 1801 having different shape and/or height. Such a system can further comprise a plurality of distracting inserts 1806, having inserts corresponding to cavities of the bodies 1801, and having different heights to achieve different amounts of distraction. Methods in accordance with embodiments of the present invention can apply such systems so that a physician can select implant components appropriate to the patient at the time of surgery, and can further substitute different bodies and/or different distracting inserts based on evaluation or reevaluation during surgery.

Figure 21A:
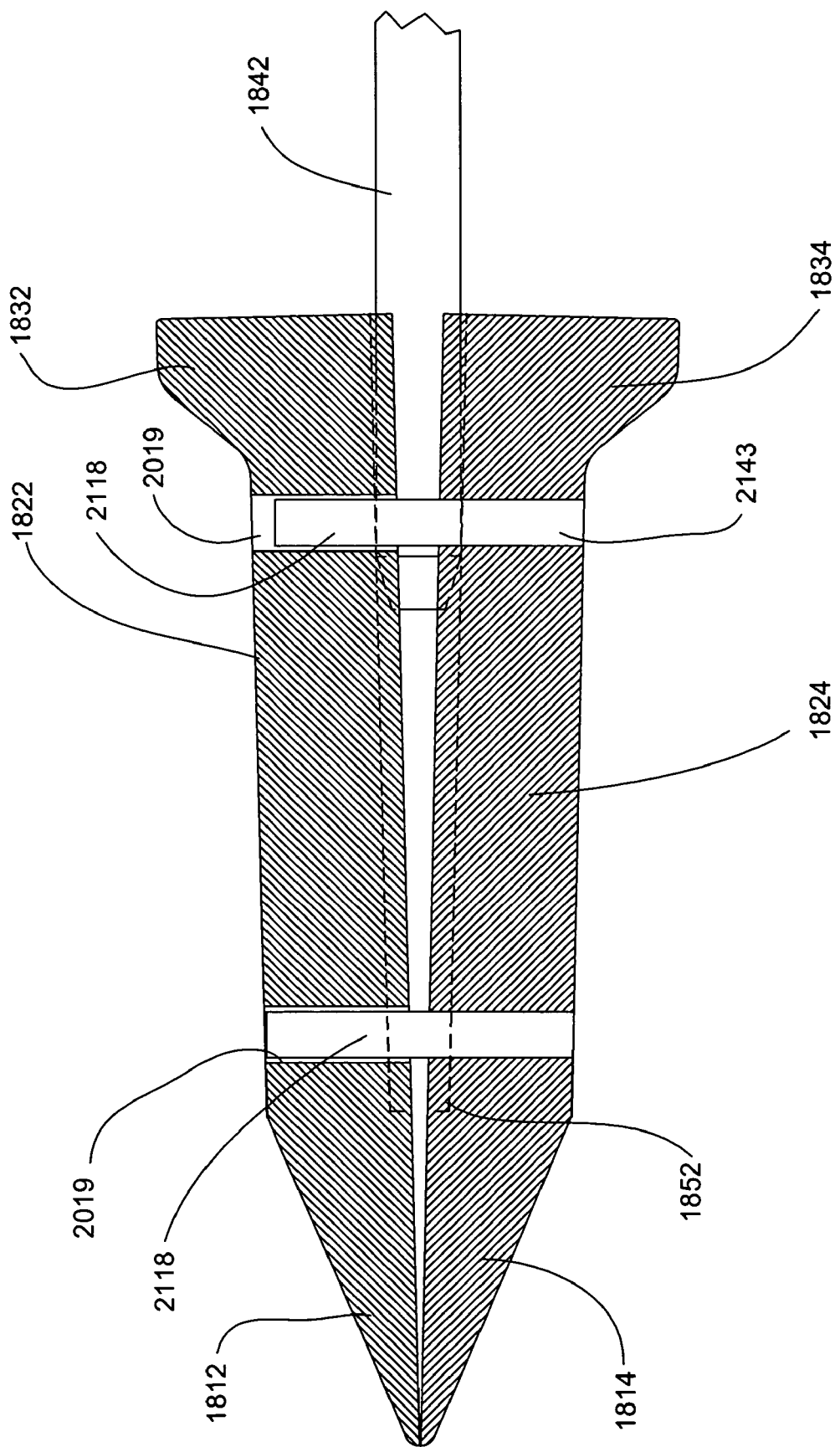
FIG. 21A is a cross-sectional side view of the implant of FIG. 18 showing a distracting insert partially inserted in a cavity of the implant having pins for aligning a first portion with a second portion.
Figure 21B:
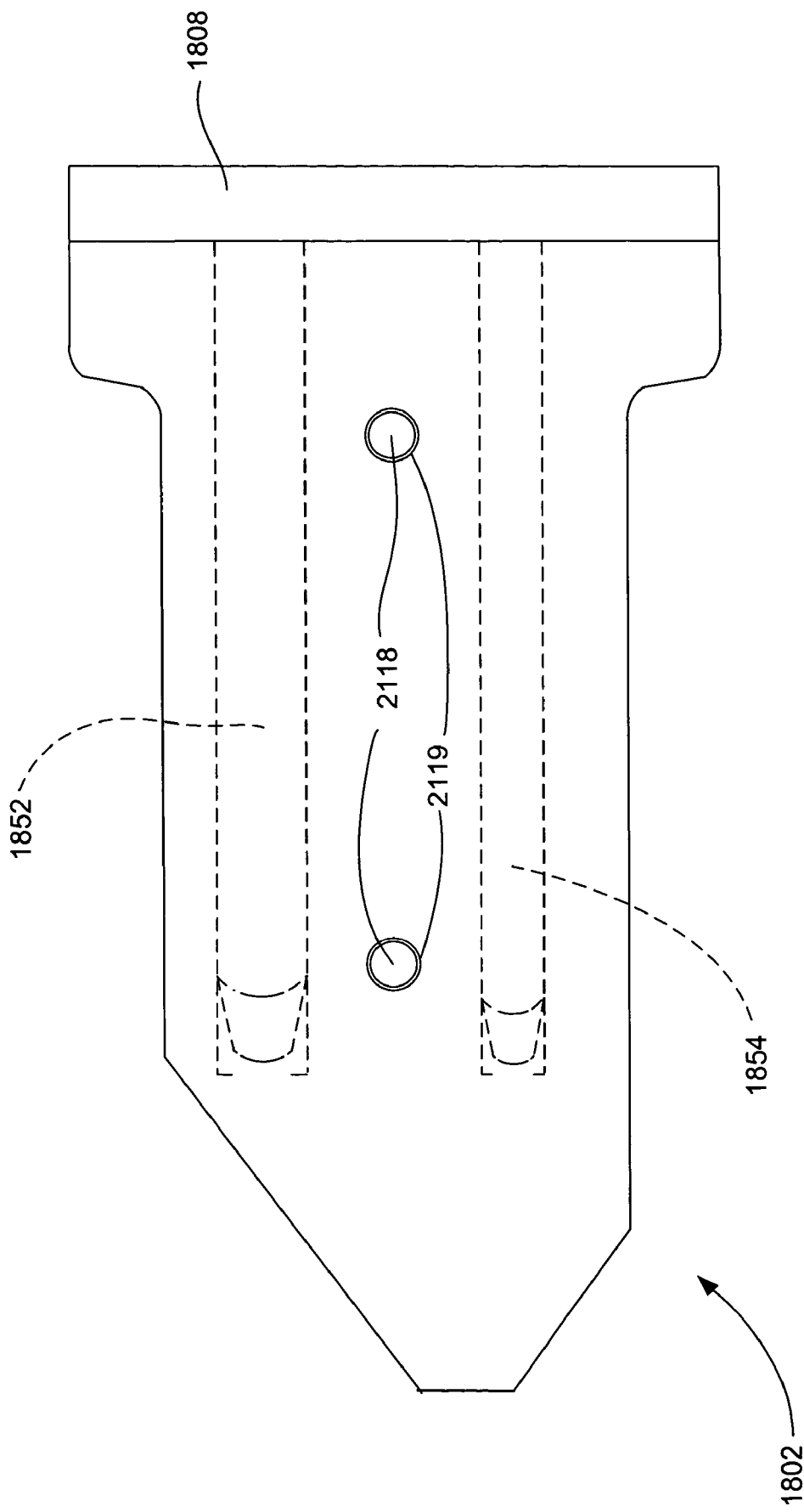
FIG. 21B is a top view of the implant of FIG. 21A showing positioning of pins for alignment of the first part and second part.

FIG. 21A is a cross-sectional side view of a distractible implant 1800 in accordance with one embodiment of the present invention positioned between adjacent spinous processes, and having an insert 1842 of the distracting insert 1806 partially inserted within a cavity 1852 of the body 1801. As described above, when inserted between spinous processes, the first part 1802 of the body 1801 is aligned and abutted with the second part 1804 of the body 1801. The first part 1802 and second part 1804 should remain aligned while the body 1801 is inserted between the spinous processes, and further should remain aligned while the distracting insert 1806 is mated with the body 1801. In order to maintain proper alignment, one of the first and second parts 1802,1804 can include alignment pins (or protrusions) 2118 that mate with corresponding holes 2119 of the other of the first and second parts 1802,1804. The pins 2118 can be made of the same or different material as the body 1801, and can be integrally formed or mated with the corresponding part. For example, where the pins 2118 are made of titanium, and the body 1801 is made of a biocompatible thermoplastic, the pins 2118 can be press fit into the second part 1804. The pins 2118 are free to slide in and out of the holes 2119, but are prevented from separating from the holes 2119 by pressure of the spinous processes. As an insert 1842 enters a cavity 1852 of the body 1801, the distal end of the body 1801 begins to separate, as shown. As the spinous processes are distracted, the pins 2118 move within the holes 2119, allowing separation of the first part 1802 and second part 1804. The pins 2118 prevent relative shifting or sliding along the longitudinal axis or along the length of the spinous process. The pins 2118 (and corresponding holes 2119) preferably have a height larger than the maximum distraction height, thereby preventing the pins 2118 from separating from the holes 2119 and allowing relative shifting of the first and second parts 1802,1804. FIG. 21B is a top view showing the position of the pins 2118 relative to a first and second cavity 1852,1854. Two pins 2118 are shown extending through holes 2119 of the second part 1802, however, in other embodiments, any number of pins 2118 or protrusions can be integrally formed or connected with one of the first and second parts 1802,1804.

In an alternative embodiment (not shown), the first part 1802 and second part 1804 of the body 1801 can be bound together by a flexible, artificial ligament or suture material. For example, the material can be a bio-compatible polymer having flexible properties. The artificial ligament or suture material can limit the shifting between the first part 1802 and second part 1804. In still other embodiments, some other device can be employed to maintain alignment of the first and second parts 1802,1804. It is intended that in some embodiments of the present invention, it is preferable to maintain alignment of the first and second parts 1802,1804 during distraction. As one of ordinary skill in the art can appreciate, many different devices can be employed to maintain alignment between the first and second parts 1802,1804 of the body 1801.

Figure 22A:
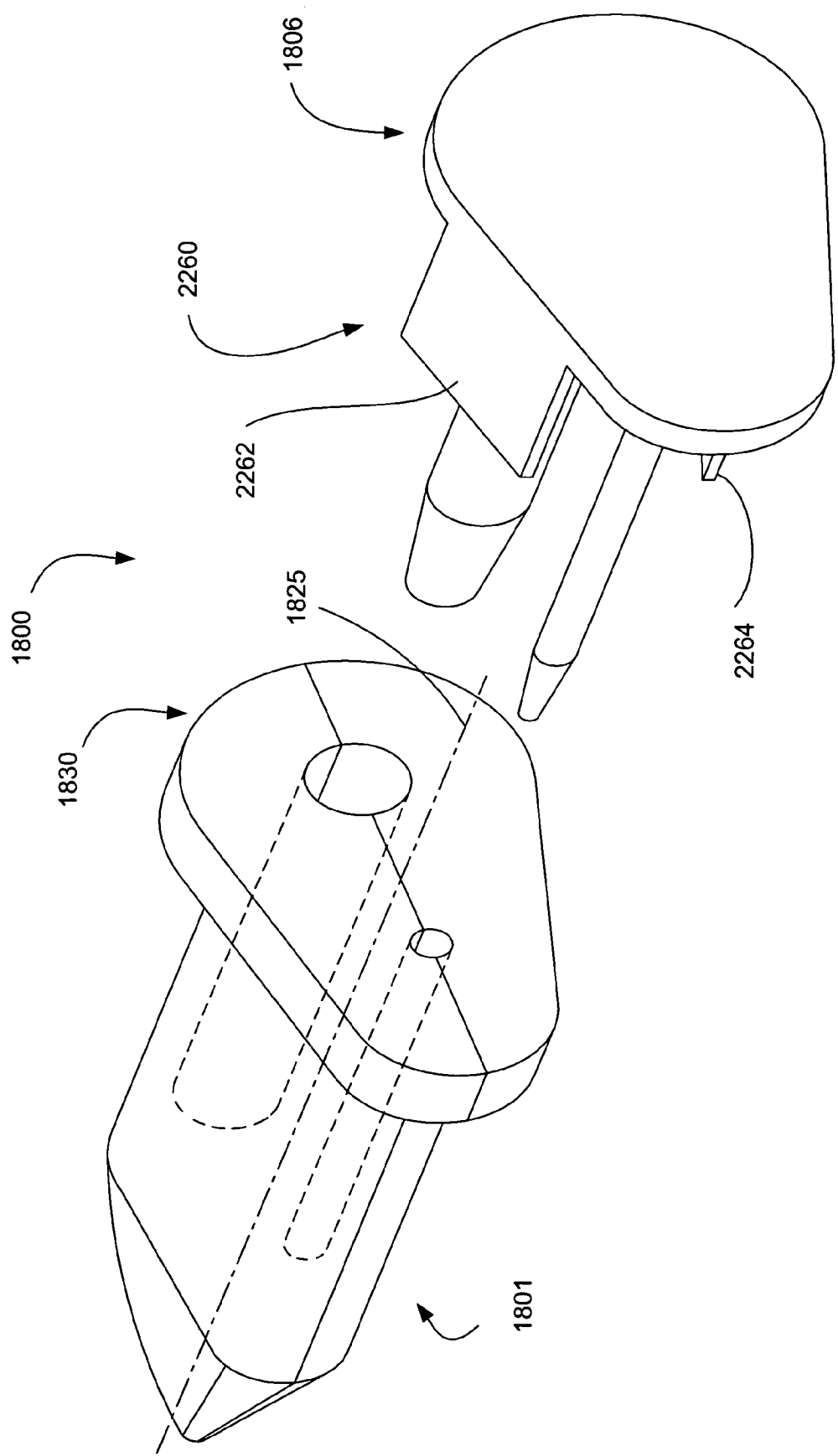
FIG. 22A is a perspective view of an alternative embodiment of an implant for use with systems and methods of the present invention, wherein the distracting insert includes a clip.
Figure 22B:
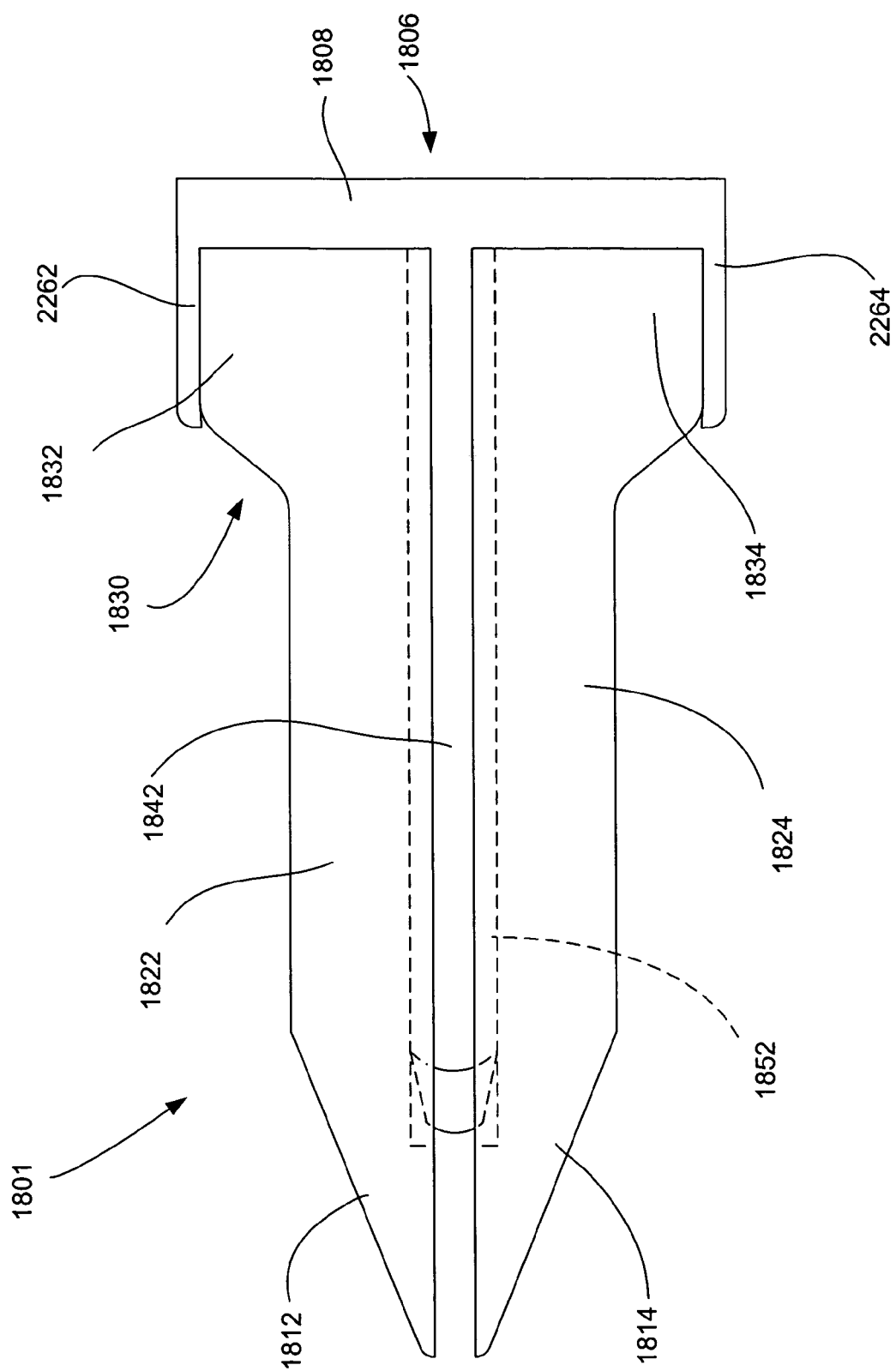
FIG. 22B is a side view of the implant of FIG. 22A showing a distracting insert mated with the implant.

As shown in FIGS. 22A and 22B, the distracting insert 1806 can be secured to the body 1801 by a clip 2260. The body 1801 as shown in FIGS. 22A-22D is the same as the body 1801 of FIG. 18. Commonly labeled components are as described above. However, it should be noted that other embodiments of a body 1801 can be used with distracting inserts 1806 described with reference to FIG. 22A-22D. In one embodiment, the clip 2260 can include a first tab 2262 and a second tab 2264. Each tab 2262,2264 can extend across at least a portion of the width of the respective portion of the wing 1830 along the longitudinal axis 1825. When the distracting insert 1806 is mated with the body 1801, the wing 1830 can be interference-fit with the distracting insert 1806 so that the wing 1830 is held between the tabs 2262,2264. The pressure applied to the surfaces of the wing 1830 should create sufficient frictional force to prevent relative movement between the body 1801 and distracting insert 1806. In other embodiments, the clip 2260 can comprise a single lip along a portion of, or the entire periphery of the cap (and wing 1830) and can extend across at least a portion of the width of the wing 1830 along the longitudinal axis 1825.

Figure 22C:
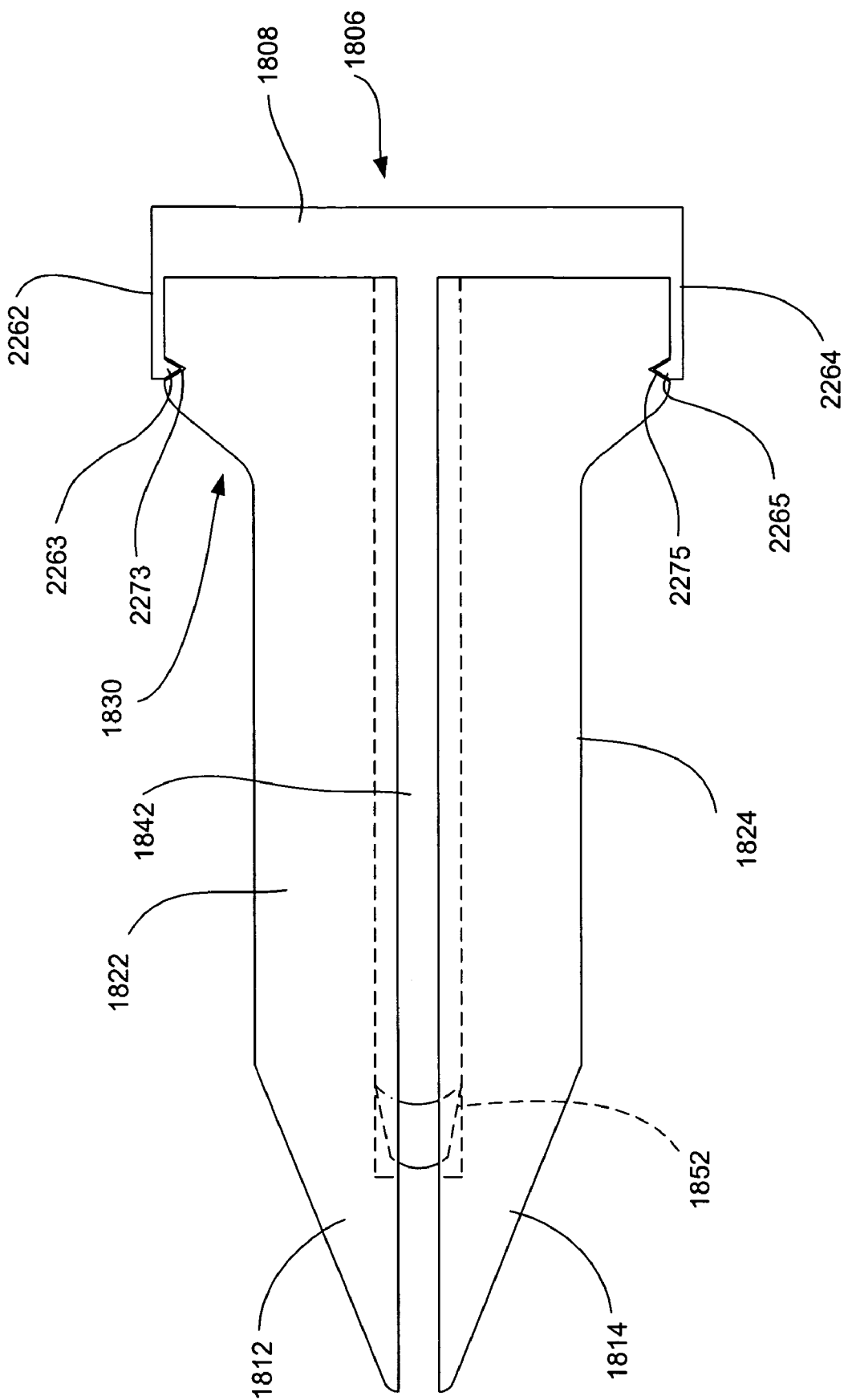
FIG. 22C is a side view of an alternative embodiment of an implant mated with an alternative embodiment of a distracting insert.

As shown in FIG. 22C, in still other embodiments, each tab 2262,2264 can include a protrusion 2263,2265 located at a proximal end of the tab 2262,2264. The wing 1830 can include indentations 2273,2275, or cavities, for receiving each of the protrusions 2263,2265 so that when the protrusions are positioned within the respective indentations, the clip 2260 is locked in place. Alternatively, the tab 2262,2264 can extend beyond a ledged wing 1830, so that the clip 2260 can be locked in place when the protrusions 2263,2265 clear the wing 1830. As described above, the distracting insert 1806 is mated with the positioned body 1801 by gradually urging the inserts of the distracting insert 1806 along the length of the cavities of the spacer 1820. The protrusions 2263,2265 can be beveled, so that as the protrusions contact an outer lip of the wing 1830, the tabs 2262,2264 deflect upward, allowing the distracting insert 1806 to continue moving into position along the longitudinal axis. When the protrusions 2263,2265 find the indentations 2273,2275 of the wing 1830 (or alternatively, when the protrusions clear the ledge), the clasp 2260 locks into place and the distracting insert 1806 is mated with the body 1801.

Figure 22D:
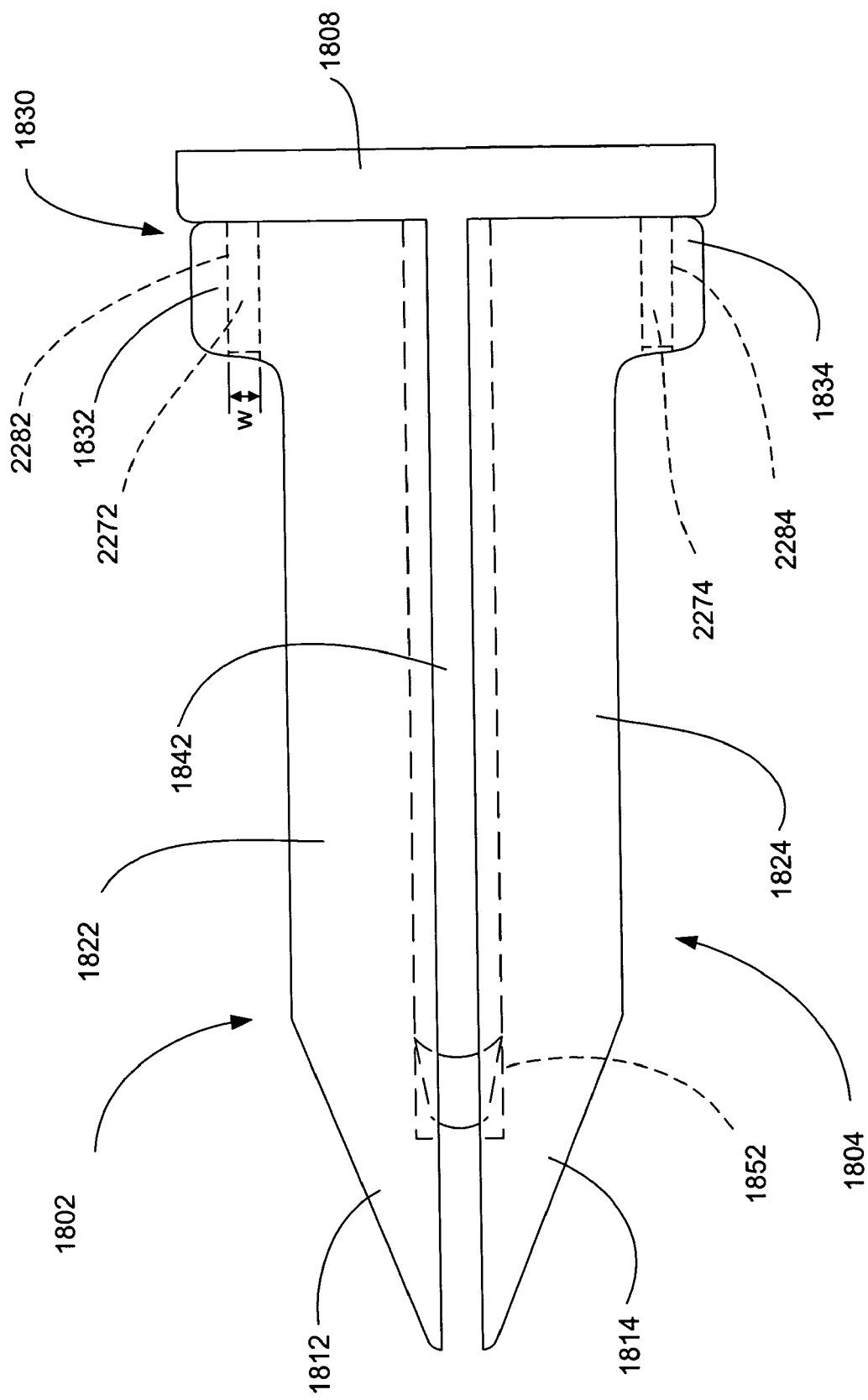
FIG. 22D is a side view of still another embodiment of an implant mated with still another embodiment of a distracting insert.

In still further embodiments, the distracting insert 1806 need not include a clip, but can be mated with the body 1801 using some other device. For example, as shown in FIG. 22D, an insert 1842 can include one or more pegs 2272,2274, and one or more corresponding through-holes 2282,2284 (or cavities) within the first wing 1830. The one or more pegs 2272,2274 can be sized such that a feature of the one or more pegs 2272,2274 is approximately the same width, or slightly larger than a width, w, of the one or more corresponding through-holes 2282,2284, so that an interference fit is created between the distracting insert 1806 and the body 1801, holding the distracting insert 1806 seated in place, and limiting the relative movement of the first part 1802 and second part 1804.

Figure 23:
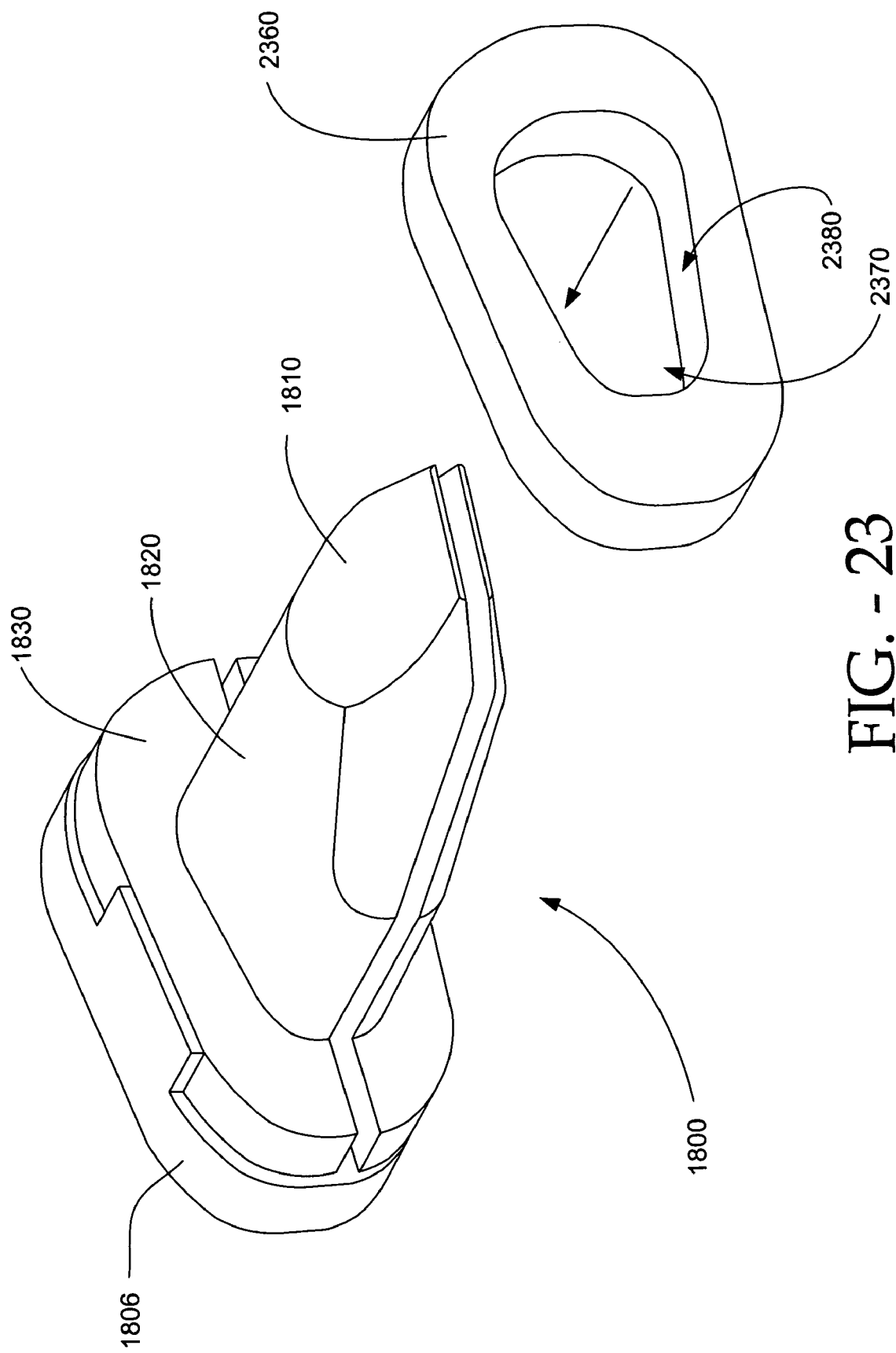
FIG. 23 is a perspective view of an embodiment of a distractible implant in accordance with the present invention having a second wing for limiting or blocking shifting along the longitudinal axis.

Referring to FIG. 23, the implant 1800 can further include a second wing 2360, similar to previously described embodiments. The second wing 2360 can be connected to the proximal end of the spacer 1820 so that portions of the adjacent spinous processes are sandwiched between the second wing 2360 and the first wing 1830. The second wing 2360, like the first wing 1830, can prevent lateral displacement of the body 1801 relative to the spinous processes. The second wing 2360 can be teardrop-shaped and sized to approximate the shape and size of the first wing 1830 when the distracting insert 1806 is mated with the body 1801. Likewise, the sides of the second wing 2360 define a space 2370 with a lip 2380 that allows the second wing 2360 to pass over the distraction guide 1810 to meet and connect with the spacer 1820. The space 2370 defined within the second wing 2360 should correspond with the distracted height of the body 1801. As described above, systems and methods in accordance with the present invention can comprise a plurality of bodies 1801 and a plurality of distracting inserts 1806 to suit a particular patient. Likewise, systems and methods in accordance with the present invention can further comprise a plurality of second wings 2360 corresponding in size and shape to the plurality of bodies 1801 and the plurality of distracting inserts 1806. The second wing 2360 can be secured to the spacer 1820, for example as described above. The second wing 2360 is implanted once the distraction guide 1810, spacer 1820, and first wing 1830 are inserted as a unit between the spinous processes of adjacent cervical vertebrae.

It is to be understood that the various features of the various embodiments can be combined with other embodiments of the invention and be within the spirit and scope of the invention. Thus, for example only, the embodiment of FIG. 18 can have truncated wings as depicted in other embodiments.

Materials for use in Implants of the Present Invention

It is to be understood that implants in accordance with the present invention, and/or portions thereof can be fabricated from somewhat flexible and/or deflectable material. In these embodiments, the implant and/or portions thereof can be made out of a polymer, such as a thermoplastic. For example, in one embodiment, the implant can be made from polyketone, known as polyetheretherketone (PEEK). Still more specifically, the implant can be made from PEEK 450G, which is an unfilled PEEK approved for medical implantation available from Victrex of Lancashire, Great Britain. Other sources of this material include Gharda located in Panoli, India. PEEK has the following approximate properties:

Property Value

Density 1.3 g/cc

Rockwell M 99

Rockwell R 126

Tensile Strength 97 MPa

Modulus of Elasticity 3.5 GPa

Flexural Modulus 4.1 GPa

The material specified has appropriate physical and mechanical properties and is suitable for carrying and spreading a physical load between the adjacent spinous processes. The implant and/or portions thereof can be formed by extrusion, injection, compression molding and/or machining techniques.

In some embodiments, the implant can comprise, at least in part, titanium or stainless steel, or other suitable implant material which is radiopaque, and at least in part a radiolucent material that does not show up under x-ray or other type of imaging. For example, in one embodiment, a first wing, a second wing and a shaft can comprise a radiopaque material (e.g., titanium) and a rotatable spacer and a lead-in tissue expander can comprise a radiolucent material (e.g., PEEK). In such an embodiment, under imaging the implant looks like an "H". The physician can have a less obstructed view of the spine under imaging, than with an implant comprising radiopaque materials entirely. However, the implant need not comprise any radiolucent materials.

It should be noted that the material selected can also be filled. For example, other grades of PEEK are also available and contemplated, such as 30% glass-filled or 30% carbon-filled, provided such materials are cleared for use in implantable devices by the FDA, or other regulatory body. Glass-filled PEEK reduces the expansion rate and increases the flexural modulus of PEEK relative to that which is unfilled. The resulting product is known to be ideal for improved strength, stiffness, or stability. Carbon-filled PEEK is known to enhance the compressive strength and stiffness of PEEK and lower its expansion rate. Carbon-filled PEEK offers wear resistance and load carrying capability.

In this embodiment, as described above, the implant is manufactured from PEEK, available from Victrex. As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. The spacer can also be comprised of polyetherketoneketone (PEKK). Other material that can be used include polyetherketone (PEK), polyetherketoneetherketoneketone (PEKEKK), and polyetheretherketoneketone (PEEKK), and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials." Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

Methods for Implanting Interspinous Implants

Figure 24:
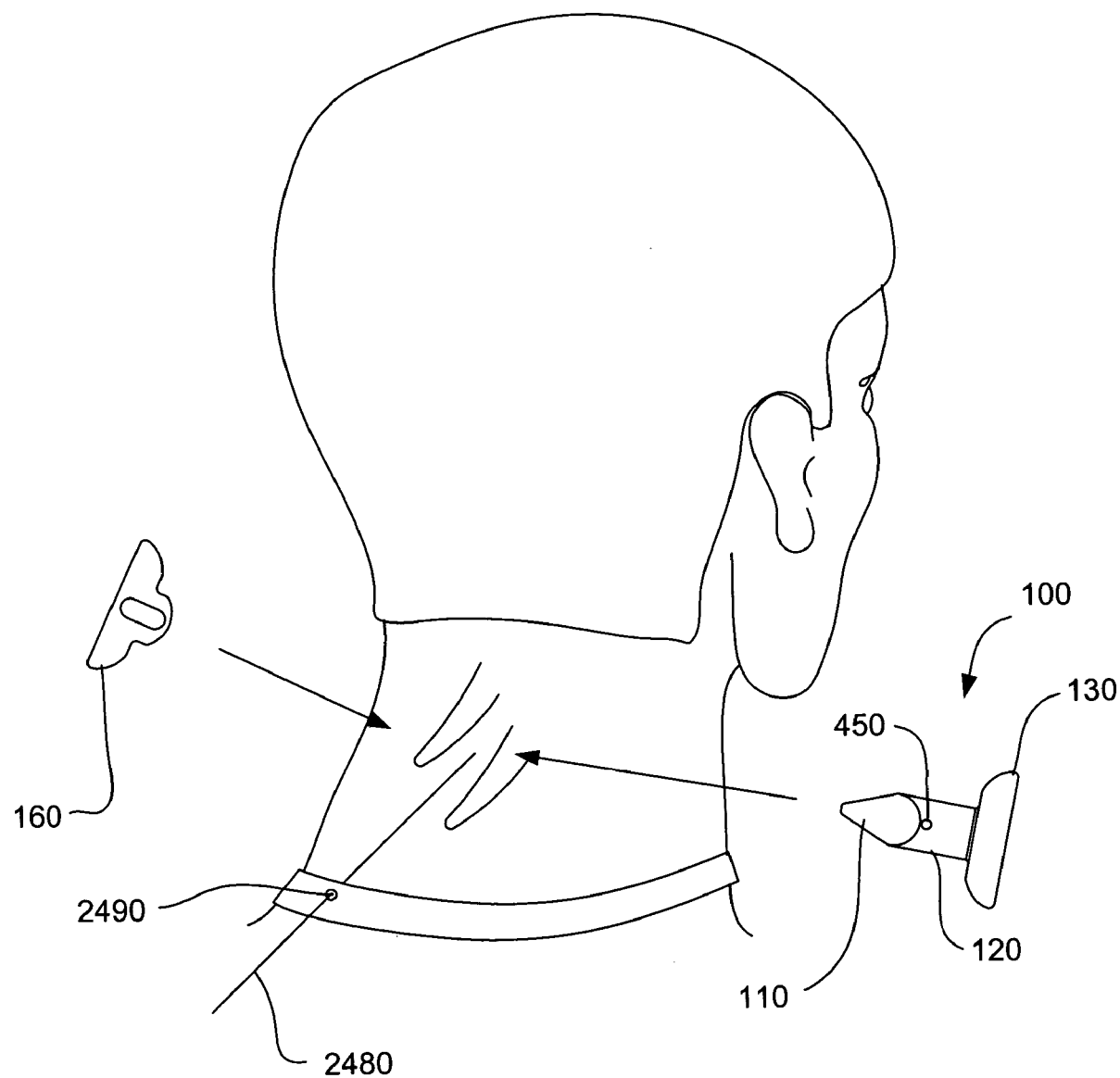
FIG. 24 illustrates an embodiment of a method for implanting an interspinous implant in accordance with the present invention.

A minimally invasive surgical method for implanting an implant 100,1800 in the cervical spine is disclosed and taught herein. In this method, as shown in FIG. 24, preferably a guide wire 2480 is inserted through a placement network 2490 into the neck of the implant recipient. The guide wire 2480 is used to locate where the implant is to be placed relative to the cervical spine, including the spinous processes. Once the guide wire 2480 is positioned with the aid of imaging techniques, an incision is made on the side of the neck so that an implant in accordance with an embodiment of the present invention, can be positioned in the neck thorough an incision and along a line that is about perpendicular to the guide wire 2480 and directed at the end of the guide wire 2480. In one embodiment, the implant can be a sized implant 100 (i.e., having a body that is not distractable), such as described above in FIGS. 1-17 and including a distraction guide 110, a spacer 120, and a first wing 130. The implant 100 is inserted into the neck of the patient. Preferably during insertion, the distraction end pierces or separates the tissue without severing the tissue.

Once the implant 100 is satisfactorily positioned, a second wing 160 can be optionally inserted along a line that is generally colinear with the line over which the implant 100 is inserted but from the opposite side of the neck. The anatomy of the neck is such that it is most convenient and minimally invasive to enter the neck from the side with respect to the implant 100 and the second wing 160. The second wing 160 is mated to the implant and in this particular embodiment, the second wing 160 is snapped into engagement with the implant 100. In an alternative embodiment, the second wing 160 is attached to the implant by the use of a fastener, for example by a screw 450. Where a screw is used, the screw 450 can be positioned using a screw driving mechanism that is directed along a posterior to anterior line somewhat parallel to the guide wire 2480. This posterior to anterior line aids the physician in viewing and securing the second wing 160 to the implant.

Figure 25:
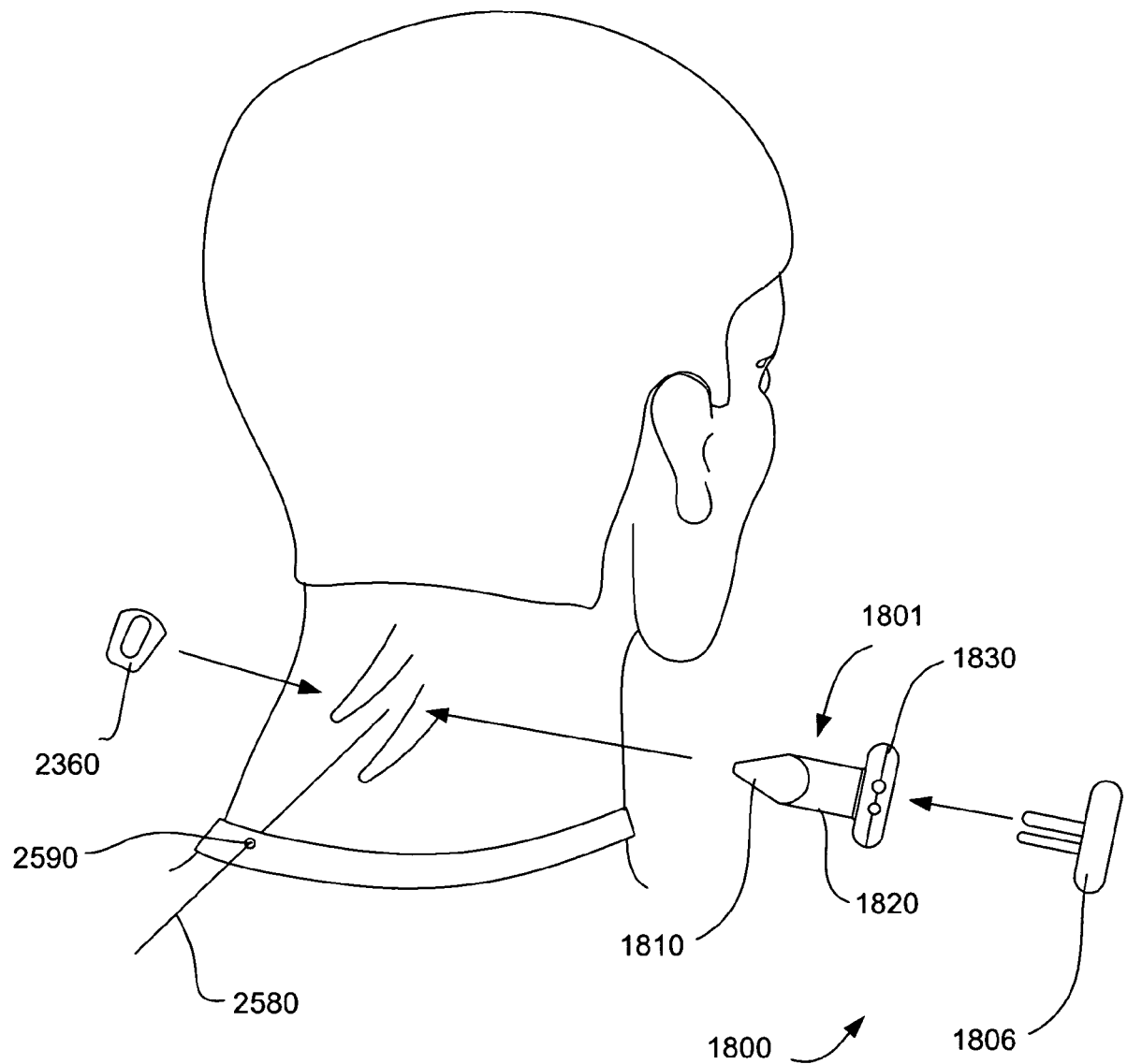
FIG. 25 illustrates an alternative embodiment of a method for implanting an interspinous implant in accordance with the present invention.

In other embodiments of methods in accordance with the present invention, the implant can be a distractible implant 1800, such as described above in FIGS. 18-23. In such embodiments, as shown in FIG. 25, preferably a guide wire 2580 is inserted through a placement network 2590 into the neck of the implant recipient (as shown and described above). Once the guide wire 2580 is positioned with the aid of imaging techniques, an incision is made on the side of the neck so that a distractible body 1801 in accordance with an embodiment of the present invention, can be positioned in the neck thorough an incision and along a line that is about perpendicular to the guide wire 880 and directed at the end of the guide wire. The distractible body 1801 can include a distraction guide 1810, a spacer 1820, and a first wing 1830. The body 1801 is inserted into the neck of the patient, between adjacent spinous processes. Preferably during insertion, the distraction guide 1810 pierces or separates the tissue without severing the tissue, and the body 1801 is positioned so that the spacer 1820 is between the adjacent spinous processes. A distracting insert 1806 is then positioned within the incision and urged into one or more cavities of the body 1801, distracting the spinous processes between which the body is positioned. As the distracting insert 1806 mates with the body 1801, the distracting insert 1806 locks in place.

Once the distractible implant 1800 is satisfactorily positioned and distracted, a second wing 2360 can optionally be inserted along a line that is generally colinear with the line over which the body 1801 is inserted but from the opposite side of the neck. The anatomy of the neck is such that it is most convenient and minimally invasive to enter the neck from the side with respect to the body 1801 and the second wing 2360. The second wing 2360 can be mated to the body 1801 through an interference fit, or alternatively by attaching to the body 1801 by the use of a fastener, or by some other device, as described above. For example, where a screw is employed, the screw can be positioned using a screw driving mechanism that is directed along a posterior to anterior line somewhat parallel to the guide wire. This posterior to anterior line aids the physician in viewing and securing the second wing 2360 to the body 1801.

The foregoing description of the present invention have been presented for purposes of illustration and description. It is not intended to be exhaustive or to limit the invention to the precise forms disclosed. Many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed:

1. A method for insertion of an interspinous implant between spinous processes comprising the steps of:
accessing first and second spinous processes;
inserting a body between the spinous processes, which body includes a first part and a second part;
inserting a distracting insert between the first part and the second part in order to distract the first part and the second part apart and in order to cojoin the first part and the second part;
wherein inserting the distracting insert between the first part and the second part comprises inserting an insert that extends from the distracting insert into a groove formed within the body, the insert including a greater height than the groove thereby urging apart the first and second parts.

2. The method of claim 1, further comprising:
seating the distracting insert with the body; and
forming an interference fit between the distracting insert and the body.

3. The method of claim 1, further comprising moving a distraction guide between the spinous processes, the distraction guide including a wedge shape with a narrow tip positioned at a proximal end of the body.

4. The method of claim 1, further comprising positioning a wing located on a distal end of the body against lateral sides of the spinous processes, the wing including a greater height than the body.

5. The method of claim 4 wherein the wing is a first wing and the method further comprises positioning a second wing on the body and positioning a portion of the spinous processes between the first wing and a second wing.

6. The method of claim 1 further comprising inserting a second insert that extends from the distracting insert into a second groove formed within the body, the second insert including a smaller height than the insert.

7. The method of claim 1, wherein the step of accessing first and second spinous processes includes laterally accessing the first and second spinous processes.

8. The method of claim 1, further comprising inserting the distracting insert and creating a gap between the first part and the second part.

9. The method of claim 8, further comprising maintaining an area of contact between the first part and the second part.

10. The method of claim 1 further comprising inserting the body and moving the body towards the spinous processes and separating tissue without severing the tissue with a distractor positioned at a leading end of the body.

11. The method of claim 1, further comprising inserting the body between the spinous processes and positioning grooves in the body in a lateral direction.

12. A method for insertion of an interspinous implant between spinous processes comprising the steps of:
accessing first and second spinous processes;
inserting a body between the spinous processes, which body includes a first part and a second part;
inserting a distracting insert between the first part and the second part in order to cojoin the first part and the second part;
wherein inserting the distracting insert between the first part and the second part comprises inserting an insert that extends from the distracting insert into a groove formed within the body, the insert including a greater height than the groove thereby urging apart the first and second parts.

13. The method of claim 12, further comprising:
seating the distracting insert with the body; and
forming an interference fit between the distracting insert and the body.

14. The method of claim 12, further comprising positioning a wing located on a distal end of the body against lateral sides of the spinous processes, the wing including a greater height than the body.

15. The method of claim 14 wherein the wing is a first wing and the method further comprises positioning a second wing on the body and positioning a portion of the spinous processes between the first wing and a second wing.

16. The method of claim 12 further comprising inserting a second insert that extends from the distracting insert into a second groove formed within the body.

17. The method of claim 12, wherein the step of accessing first and second spinous processes includes laterally accessing the first and second spinous processes.

18. The method of claim 12, further comprising inserting the distracting insert and creating a gap between the first part and the second part.

19. The method of claim 18, further comprising maintaining contact between the first part and the second part.

20. The method of claim 12 further comprising inserting the body and moving the body towards the spinous processes and separating tissue without severing the tissue with a distractor positioned at a leading end of the body.

21. The method of claim 12, further comprising inserting the body between the spinous processes and positioning grooves in the body in a lateral direction.

22. A method for insertion of an interspinous implant between spinous processes comprising the steps of:
accessing first and second spinous processes;
inserting a body between the spinous processes, which body includes a first part and a second part;
inserting a distracting insert between the first part and the second part in order to distract the first part and the second part apart;
wherein the inserting a distracting insert between the first part and the second part comprises inserting an insert that extends from the distracting insert into a groove formed within the body, the insert including a greater height than the groove thereby urging apart the first and second parts.

23. The method of claim 22, further comprising positioning a wing located on a distal end of the body against lateral sides of the spinous processes, the wing including a greater height than the body.

24. The method of claim 23 wherein the wing is a first wing and the method further comprises positioning a second wing on the body and positioning a portion of the spinous processes between the first wing and a second wing.

25. The method of claim 22 further comprising inserting a second insert that extends from the distracting insert into a second groove formed within the body.

26. The method of claim 22, wherein the step of accessing first and second spinous processes includes laterally accessing the first and second spinous processes.

27. The method of claim 22, further comprising inserting the distracting insert and creating a gap between the first part and the second part.

28. The method of claim 27, further comprising maintaining contact between the first part and the second part.

29. The method of claim 22 further comprising inserting the body and moving the body towards the spinous processes and separating tissue without severing the tissue with a distractor positioned at a leading end of the body.

30. The method of claim 22, further comprising inserting the body between the spinous processes and positioning grooves in the body in a lateral direction.

* * * * *